(12) United States Patent  (10) Patent No.: US 7,452,325 B2
Schaller  (45) Date of Patent: Nov. 18, 2008

(54) CATHETER-BASED TISSUE REMODELING DEVICES AND METHODS

(75) Inventor: Laurent Schaller, Los Altos, CA (US)

(73) Assignee: Benvenue Medical Inc., Mt. View, CA (US)

( * ) Notice: Subject to any disclaimer, the term of this patent is extended or adjusted under 35 U.S.C. 154(b) by 207 days.

(21) Appl. No.: 11/059,866

(22) Filed: Feb. 17, 2005

(65) Prior Publication Data

US 2006/0106403 A1 May 18, 2006

Related U.S. Application Data

(60) Provisional application No. 60/627,821, filed on Nov. 15, 2004.

(51) Int. Cl.
*A61F 2/00* (2006.01)
(52) U.S. Cl. ...................................................... 600/37
(58) Field of Classification Search .................. 24/298; 604/48, 107, 264, 272, 500, 502, 506–511; 606/72, 75, 121, 139, 142–148, 157–158, 606/213, 215, 216, 222–228, 232–233; 600/16–18, 600/37
See application file for complete search history.

(56) References Cited

U.S. PATENT DOCUMENTS

| 4,841,888 A | 6/1989 | Mills et al. |
| 5,002,563 A | 3/1991 | Pyka et al. |
| 5,591,180 A | 1/1997 | Hinchliffe |
| 5,695,504 A | 12/1997 | Gifford et al. |
| 5,792,153 A | 8/1998 | Swain et al. |
| 5,797,933 A | 8/1998 | Snow et al. |
| 5,865,791 A | 2/1999 | Whayne et al. |
| 5,961,440 A | 10/1999 | Schweich, Jr. et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,079,414 A | 6/2000 | Roth |
| 6,155,968 A * | 12/2000 | Wilk ........................... 600/16 |
| 6,193,733 B1 | 2/2001 | Adams |
| 6,231,561 B1 | 5/2001 | Frazier et al. |
| 6,290,674 B1 * | 9/2001 | Roue et al. ................... 604/107 |
| 6,332,893 B1 | 12/2001 | Mortier et al. |
| 6,346,074 B1 | 2/2002 | Roth |
| 6,360,749 B1 * | 3/2002 | Jayaraman .................. 128/898 |

(Continued)

*Primary Examiner*—Samuel G Gilbert
(74) *Attorney, Agent, or Firm*—Knobbe Martens Olson & Bear LLP

(57) ABSTRACT

Devices and methods utilizing a catheter to remodel soft tissue of a patient and, in a preferred embodiment, to reduce the volume of the left ventricle of a heart. In one embodiment, one or more sutures are passed through a wall of the ventricle. The ends of the one suture and, more preferably, the multiples sutures are drawn together to draw tissue portions towards one another. In another embodiment, tissue remodeling clip is implanted into a wall of the ventricle. Ends of the clip are resiliently biased to move relative to one another to draw tissue portions towards one another. In yet another embodiment, a tissue remodeling anchor includes a base and a plurality of legs attached to the base. The legs of the tissue anchor are implanted into a wall of the ventricle and moved toward one another to draw tissue portions toward one another. A retaining member is positioned on the tissue anchor to prevent the legs from moving apart.

16 Claims, 29 Drawing Sheets

U.S. PATENT DOCUMENTS

| | | |
|---|---|---|
| 6,406,420 B1 | 6/2002 | McCarthy et al. |
| 6,461,366 B1 | 10/2002 | Seguin |
| 6,629,534 B1 | 10/2003 | St. Goar et al. |
| 6,719,767 B1 * | 4/2004 | Kimblad .................... 606/151 |
| 6,776,784 B2 | 8/2004 | Ginn |
| 6,800,081 B2 | 10/2004 | Parodi |
| 6,802,858 B2 | 10/2004 | Gambale et al. |
| 6,852,076 B2 * | 2/2005 | Nikolic et al. ................ 600/37 |
| 7,063,710 B2 | 6/2006 | Takamoto et al. |
| 7,087,064 B1 * | 8/2006 | Hyde ........................ 606/142 |
| 7,175,636 B2 | 2/2007 | Yamamoto et al. |
| 2002/0029080 A1 | 3/2002 | Mortier et al. |
| 2002/0065451 A1 | 5/2002 | Spence |
| 2002/0077524 A1 | 6/2002 | Schweich, Jr. et al. |
| 2002/0120200 A1 | 8/2002 | Brockway et al. |
| 2002/0169359 A1 | 11/2002 | McCarthy et al. |
| 2002/0173694 A1 | 11/2002 | Mortier et al. |
| 2002/0188170 A1 * | 12/2002 | Santamore et al. ............ 600/37 |
| 2003/0050685 A1 | 3/2003 | Nikolic et al. |
| 2003/0171776 A1 | 9/2003 | Adams et al. |
| 2003/0181928 A1 | 9/2003 | Vidlund et al. |
| 2004/0030382 A1 | 2/2004 | St. Goar et al. |
| 2004/0039442 A1 | 2/2004 | St. Goar et al. |
| 2004/0097865 A1 | 5/2004 | Anderson et al. |
| 2004/0116949 A1 | 6/2004 | Ewers et al. |
| 2004/0122456 A1 | 6/2004 | Saadat et al. |
| 2004/0122473 A1 | 6/2004 | Ewers et al. |
| 2004/0127913 A1 | 7/2004 | Voss |
| 2004/0127916 A1 * | 7/2004 | Bolduc et al. ................ 606/151 |
| 2004/0127917 A1 | 7/2004 | Ginn |
| 2004/0127983 A1 | 7/2004 | Mortier et al. |
| 2004/0133063 A1 | 7/2004 | McCarthy et al. |
| 2004/0138704 A1 | 7/2004 | Gambale et al. |
| 2004/0147958 A1 | 7/2004 | Lam et al. |
| 2004/0152947 A1 | 8/2004 | Schroeder et al. |
| 2004/0162568 A1 | 8/2004 | Saadat et al. |
| 2004/0162610 A1 | 8/2004 | Liska et al. |
| 2004/0167546 A1 | 8/2004 | Saadat et al. |
| 2004/0172046 A1 | 9/2004 | Hlavka et al. |
| 2004/0186566 A1 | 9/2004 | Hindrichs et al. |
| 2004/0199183 A1 | 10/2004 | Oz et al. |
| 2004/0225304 A1 | 11/2004 | Vidlund et al. |
| 2005/0075723 A1 | 4/2005 | Schroeder et al. |
| 2005/0177180 A1 * | 8/2005 | Kaganov et al. ............ 606/151 |
| 2006/0015002 A1 * | 1/2006 | Moaddeb et al. .............. 600/37 |

* cited by examiner

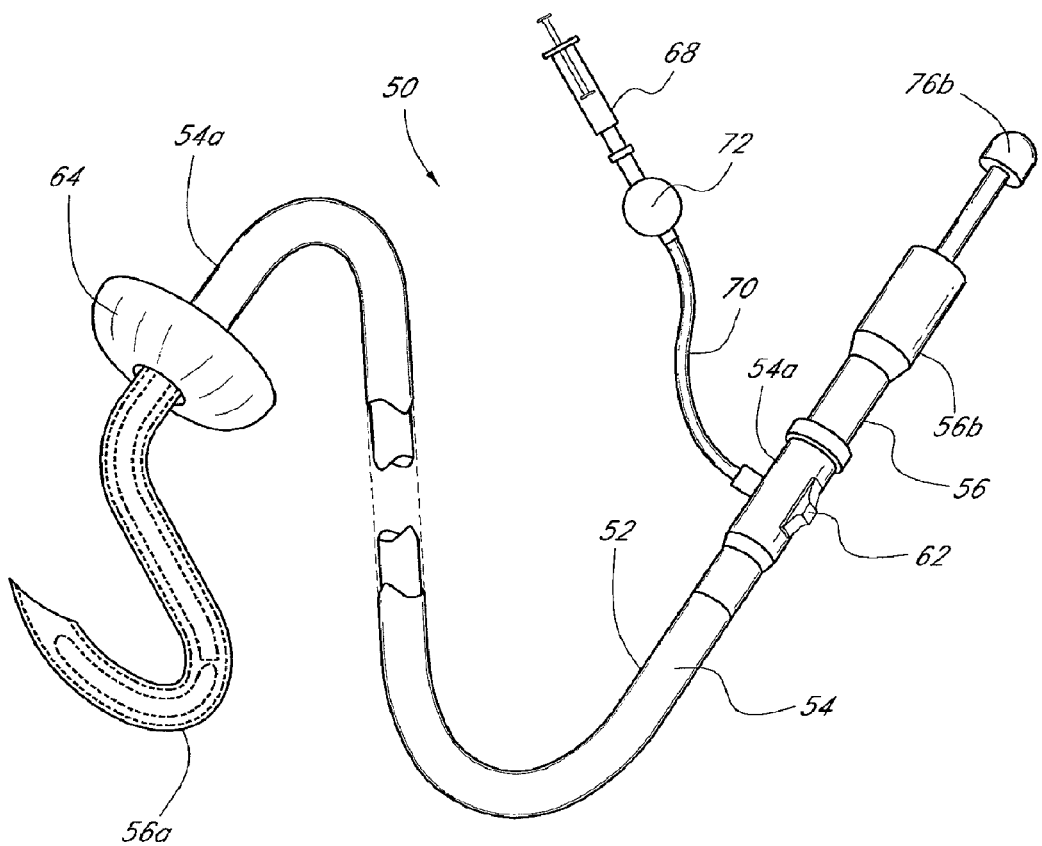
FIG.1
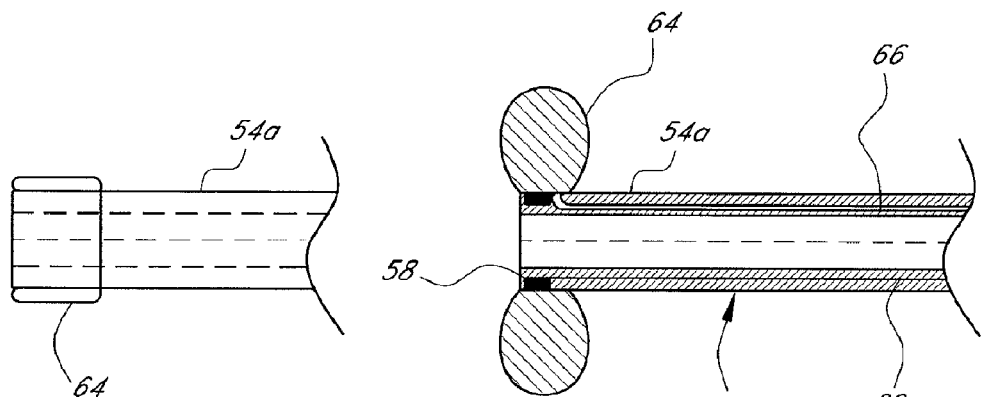
FIG.2   FIG.3

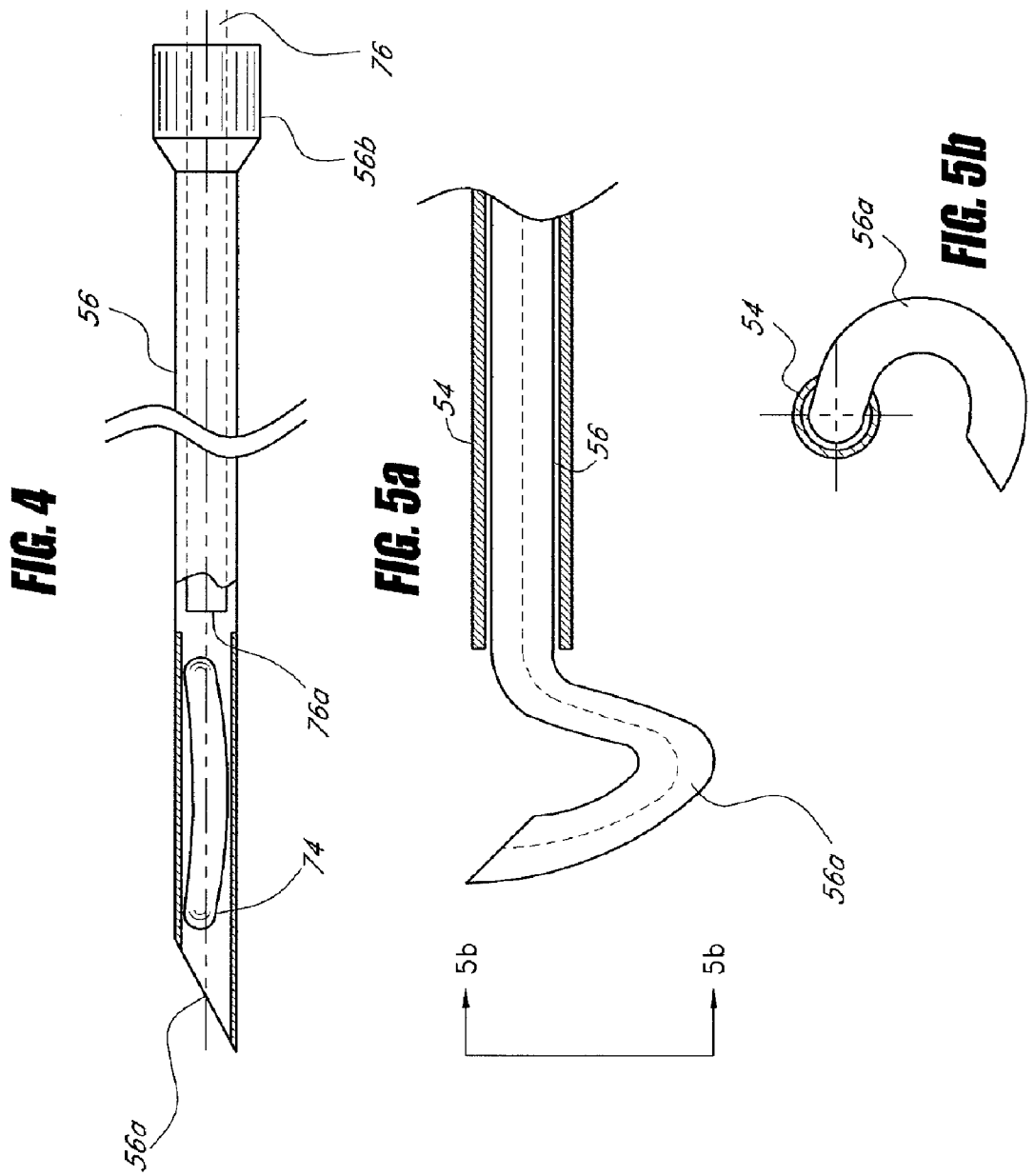

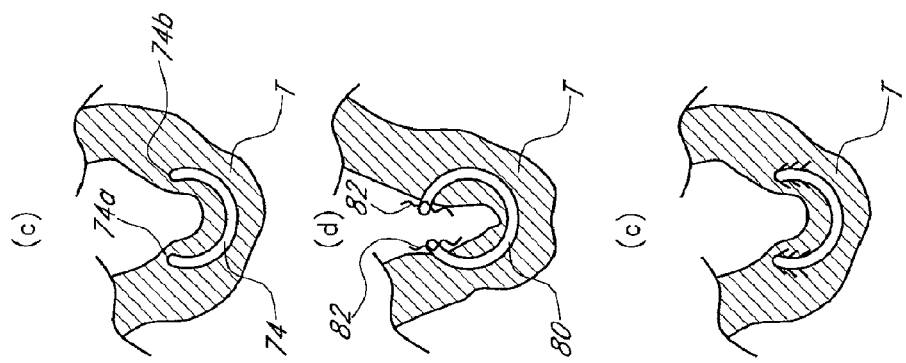
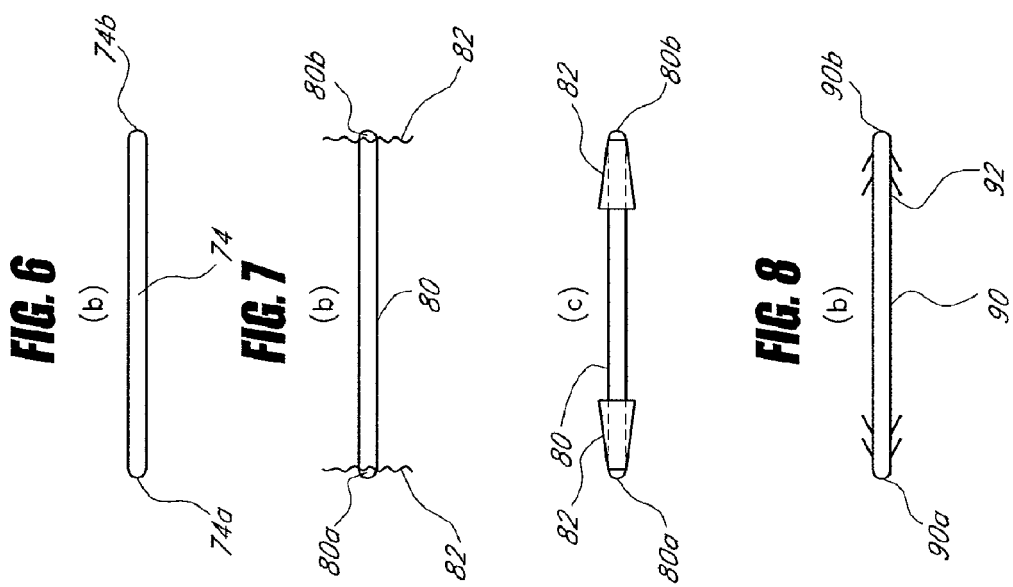
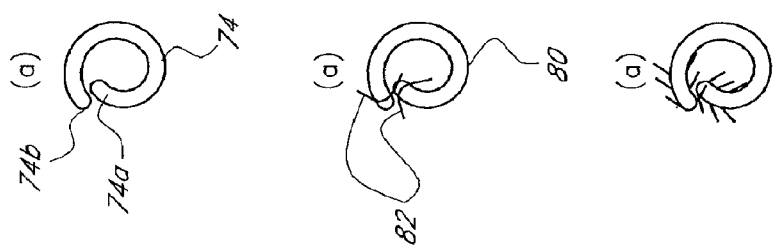

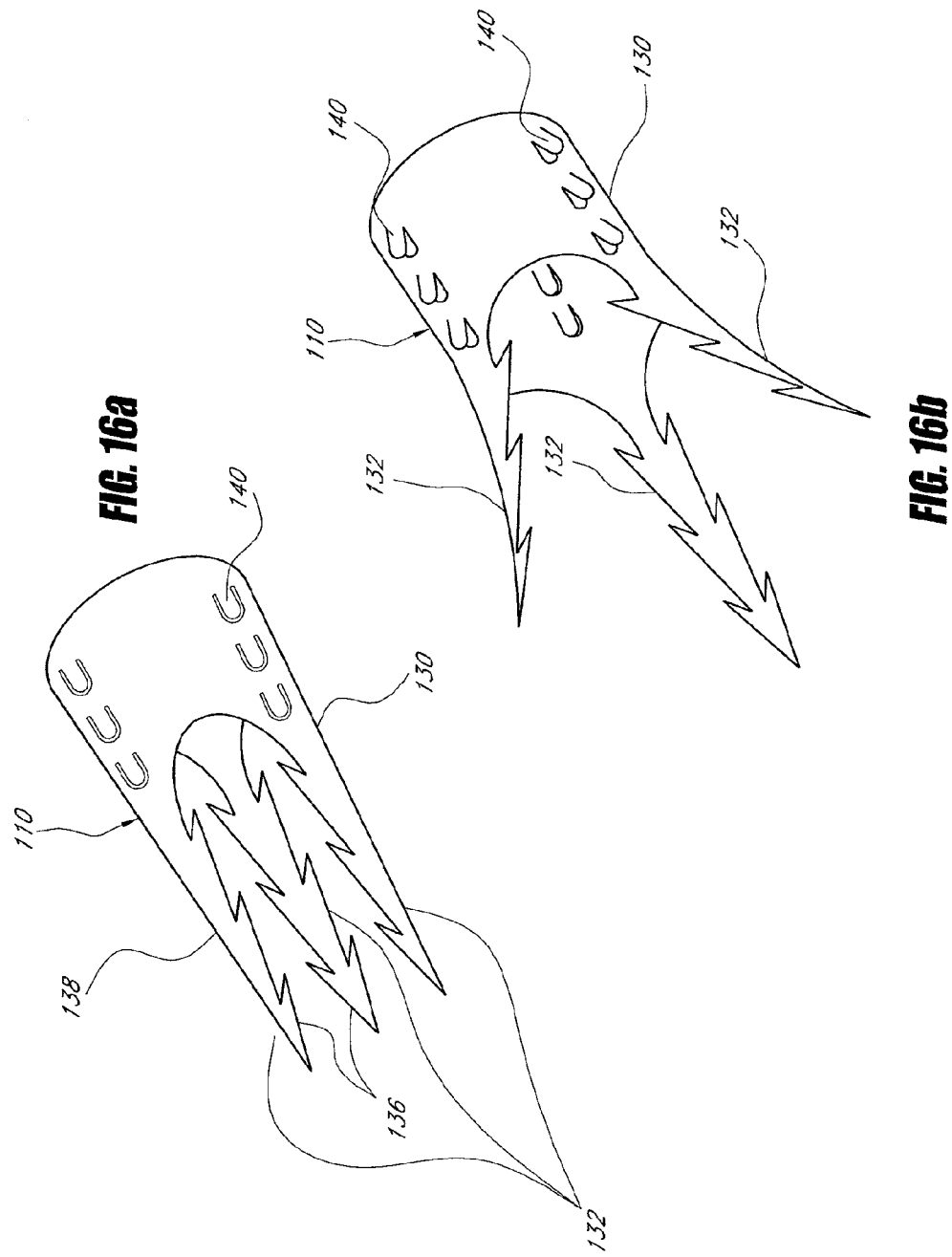

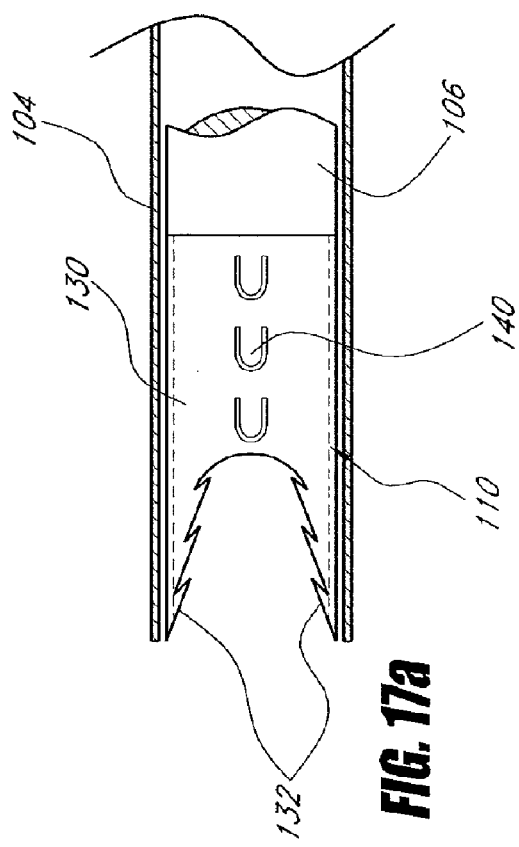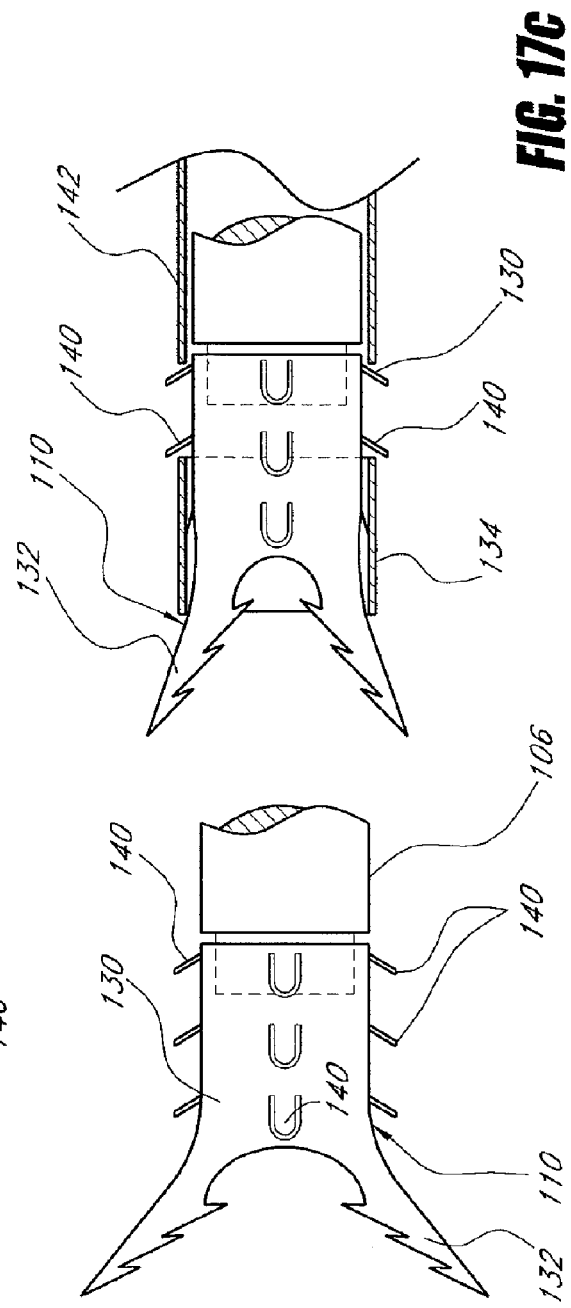
FIG. 17a
FIG. 17b
FIG. 17c

CATHETER-BASED TISSUE REMODELING DEVICES AND METHODS

RELATED APPLICATIONS

This application is related to, and claims benefit of, U.S. Provisional Patent Application No. 60/627,821, filed Nov. 15, 2004, the entirety of which is hereby incorporated by reference herein and made a part of the present disclosure.

BACKGROUND OF THE INVENTION

1. Field of the Invention

The present invention relates to methods for remodeling soft tissue of a patient and, preferably, for remodeling the left ventricle of a patient's heart. The present invention also relates to systems for accomplishing the preferred methods.

2. Description of the Related Art

Congestive heart failure is a description given to a myriad of symptoms that may be the result of the heart's inability to meet the body's demand for blood flow. Heart failure may be considered as the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure. Typically, these processes result in dilation of the left ventricular chamber.

The process of ventricular dilation may be the result of chronic volume overload or may result from a specific damage to the myocardium. In a normal heart that is exposed to long-term increased cardiac output requirements, for example, that of an athlete, there is an adaptive process of slight ventricular dilation and muscle hypertrophy. In this way, the heart compensates for the increased cardiac output requirements. With damage to the myocardium, or chronic overload, however, there are increased requirements put on the contracting myocardium to such a level that this compensated state is never achieved and the heart continues to dilate.

One condition that is likely to reduce the blood pumping efficiency of the heart muscle is ventricular dilation. As the chamber becomes enlarged, the internal surface area of the chamber increases rapidly. Blood flowing within the heart applies pressure to the internal surface of the heart chamber and because the blood applies pressure inside the heart chamber across an increased surface area, the force which must be produced by the heart in order to pump blood also increases. In many cases, the cardiac disease responsible for the ventricular dilation also limits the ability of the heart muscle to produce the increased force required to efficiently pump blood, which further compounds the problem.

In many cases, the dilation of the heart chamber becomes progressively worse and the blood pumping efficiency of the heart muscle progressively declines. As this situation worsens, the location area of compromised myocardium may bulge out as the heart contracts, further decreasing the heart's ability to move blood forward. When local wall motion moves in this way it is said to be dyskinetic. The dyskinetic portion of the myocardium may stretch and eventually form an aneurismic bulge.

There is no cure for heart failure, but it can be treated. The primary goals of treatment are to relieve symptoms and prevent worsening of the condition. Symptoms may be relieved by removing excess fluid from the body, improving blood flow and increasing delivery of oxygen to the body tissues. Medical treatment usually comprises lifestyle changes and medications. For example, diuretics have been used to reduce extra cellular fluid which accumulates in congestive heart failure patients, thereby increasing the preloaded condition of the heart. Nitrates, arteriolar vasodilators and angiotensin converting enzyme (ACE) inhibitors have been used to treat heart failure through the reduction of cardiac workload by reducing afterload. Inotropes function to increase cardiac output by increasing the force and speed of cardiac muscle contraction. These drug therapies offer some beneficial effects, but do not stop the progression of the disease.

With respect to the situation of a dilated left ventricle or aneurism bulge, a variety of surgical studies have demonstrated some clinical success of ventricular remodeling and treatment of the dilation of the infarcted ventricle. One such remodeling procedure is referred to as the Batista Procedure. In the Batista Procedure, a small portion of the enlarged lower left ventricle chamber of the heart is removed to reduce the size of the left ventricle towards normal. Typically, the Batista procedure involves the surgeon locating the left anterior descending coronary artery and making two small cuts down and outward to remove a wedge of the left ventricle. The remaining edges of the left ventricle are sewn together, returning the chamber to near its normal size. The incision is closed and the surgery is completed.

A variation of the Batista Procedure, referred to as the Dor Procedure, involves a lengthwise incision in the left ventricle along an area damaged by a myocardial infarction. The undamaged areas of the ventricle are sutured back together, eliminating the affected area. If the damaged area is too large, a patch may be used to cover the damaged area. However, in each of the Batista and Dor procedures, restoration of normal ventricular shape is a complex surgical procedure and very invasive for the patient. Furthermore, these procedures are not applicable to those patients that are not candidates for such invasive surgery.

SUMMARY OF THE INVENTION

Preferred methods of the present invention permit remodeling, tissue joining or tying of the left ventricle using a catheter-based percutaneous approach, which is far less traumatic to the patient than the Batista and Dor procedures. In addition, the methods and preferred devices disclosed herein may be adapted for use in remodeling soft tissue of a patient other than the left ventricle.

A preferred method of remodeling a ventricle of a heart includes introducing a distal portion of at least one catheter through the aorta into the ventricle. The method also includes utilizing the at least one catheter to urge tissue portions on a same side of the ventricle towards each other and to secure the tissue portions such that the volume of the ventricle is reduced.

Another preferred method of decreasing the volume of a ventricle of a heart includes providing an implant in contact with a wall of the ventricle at a contact location internal to the exterior surface of the heart and urging adjacent tissue portions located on a same side of the ventricle towards each other by applying force to the wall with the implant at the internal contact location.

Still another preferred method of reducing the volume of a ventricle of a heart includes gathering tissue by folding a pair of adjacent tissue portions of a wall of the ventricle and repeating the folding to provide a plurality of tissue folds. The gathering comprises securing the plurality of tissue folds to retain the folded portions in close proximity by advancing at least one implant through the interior of the ventricle and securing the implant to a wall of the ventricle.

A preferred embodiment is a cardiac treatment apparatus including a catheter having a catheter body configured to be introduced into a heart chamber through vasculature. The catheter includes a suture passage and a suture passing through the passage. The suture has an end portion. A tissue penetration member is movably mounted within the catheter body such that the penetration member enters an interior surface of a wall of the heart at a first location and exits the interior surface at a second location spaced from the first location. The penetration member is adapted to deliver the suture through the tissue between the locations, whereby application of tension to end portions of the suture draws the tissue locations towards each other.

Another preferred embodiment is a cardiac treatment apparatus including a catheter having a catheter body configured to be introduced into a heart chamber through vasculature. The catheter includes a clip having end portions. The clip is movably mounted in the catheter body such that one end portion enters an interior surface of a wall of the heart to introduce at least a substantial portion of the clip into the wall. An intermediate portion of the clip is embedded in the wall and the end portions are resiliently biased to move relative to each other such that the movement of the end portions draws tissue portions towards each other.

Yet another preferred embodiment is a cardiac treatment apparatus including a catheter having a catheter body configured to be introduced into a heart chamber through vasculature. The catheter includes a tissue anchor having a plurality of legs attached to a base. The legs are configured to pass through an interior surface of a wall of the heart and anchor the legs of the tissue anchor to the wall. The anchored legs have a first position upon the anchoring and are subsequently movable to a second position. The movement of the legs to the second position draws portions of tissue towards each other. The catheter also includes a retaining member for retaining the anchored legs in the second position when the catheter body is removed from the heart.

BRIEF DESCRIPTION OF THE DRAWINGS

These and other features, aspects and advantages of the present tissue remodeling devices and methods are described in greater detail below with reference to drawings of several preferred embodiments, which are intended to illustrate but not to limit the present invention. The drawings contain 40 figures.

FIG. 1 is a perspective view of a system for remodeling a left ventricle of a heart. The illustrated system includes certain features, aspects and advantages of a first embodiment. The remodeling system includes a catheter having a pair of coaxial catheter bodies.

FIG. 2 is an enlarged view of a distal end of the catheter of FIG. 1. The distal end of the catheter carries an inflatable balloon.

FIG. 3 is a cross-sectional view of the distal end of the catheter of FIG. 1, with the balloon illustrated in an inflated condition.

FIG. 4 is a partial cross-sectional view of the catheter of FIG. 1 illustrating a tissue remodeling clip that is positioned within a distal end of the inner catheter body.

FIG. 5a is a side view of the catheter in a position wherein a distal end of the inner, tissue-penetrating catheter body is extended from the outer, guide catheter body. FIG. 5b is an end view of the tissue-penetrating catheter of FIG. 5a as viewed in the direction of the arrow 5b of FIG. 5a.

FIGS. 6a-c are several views of a first embodiment of the tissue remodeling clip illustrating several positions of the clip. FIG. 6a is a view of the clip in a relaxed position. FIG. 6b is a view of the clip in a biased position and, in particular, a substantially straightened position that may occur when the clip is docked within the catheter. FIG. 6c is a view of the clip implanted within soft tissue in a tissue remodeling position.

FIGS. 7a-d are several views of a modification of the clip of FIG. 6, wherein the ends of the clip include pledgets. FIG. 7a is a view of the clip in a relaxed position. FIG. 7b is a view of the clip in a straightened position with its end pledgets in an expanded orientation. FIG. 7c is a view of the clip in a straightened position and its end pledgets in a collapsed position. FIG. 7d is a view of the clip implanted within soft tissue in a tissue remodeling position.

FIGS. 8a-c are several views of yet another modification of the clip of FIG. 6 in several positions. FIG. 8a is a view of the clip in a relaxed position. FIG. 8b is a view of the clip in a straightened position. FIG. 8c is a view of the clip implanted in soft tissue in a tissue remodeling position.

FIG. 11 consists of several views illustrating several steps of a preferred method of using the catheter-based system of FIG. 1.

FIG. 16a is a perspective view of the collapsible tissue anchor in a collapsed position. FIG. 16b is a perspective view of the tissue anchor in a relaxed position.

FIG. 17 includes several views of the tissue anchor being deployed from the anchor delivery catheter. FIG. 17a is an enlarged, partial cross-sectional view of the tissue anchor docked within a distal end of the delivery catheter. FIG. 17b is a view of the tissue anchor deployed from the delivery catheter and assuming a relaxed position. FIG. 17c is a view of a retaining member delivered onto the tissue anchor to retain the tissue anchor in a tissue remodeling position.

FIG. 31a is a cross-sectional view of a distal end portion of the suture cutting catheter. FIG. 31b is an end view of the suture cutting catheter. FIG. 31c is a cross-sectional view of the suture cutting catheter taken along view line 31c-31c of FIG. 31a.

FIG. 34b is an enlarged view of the catheter of FIG. 34a.

DETAILED DESCRIPTION OF THE PREFERRED EMBODIMENT

Figure 9:
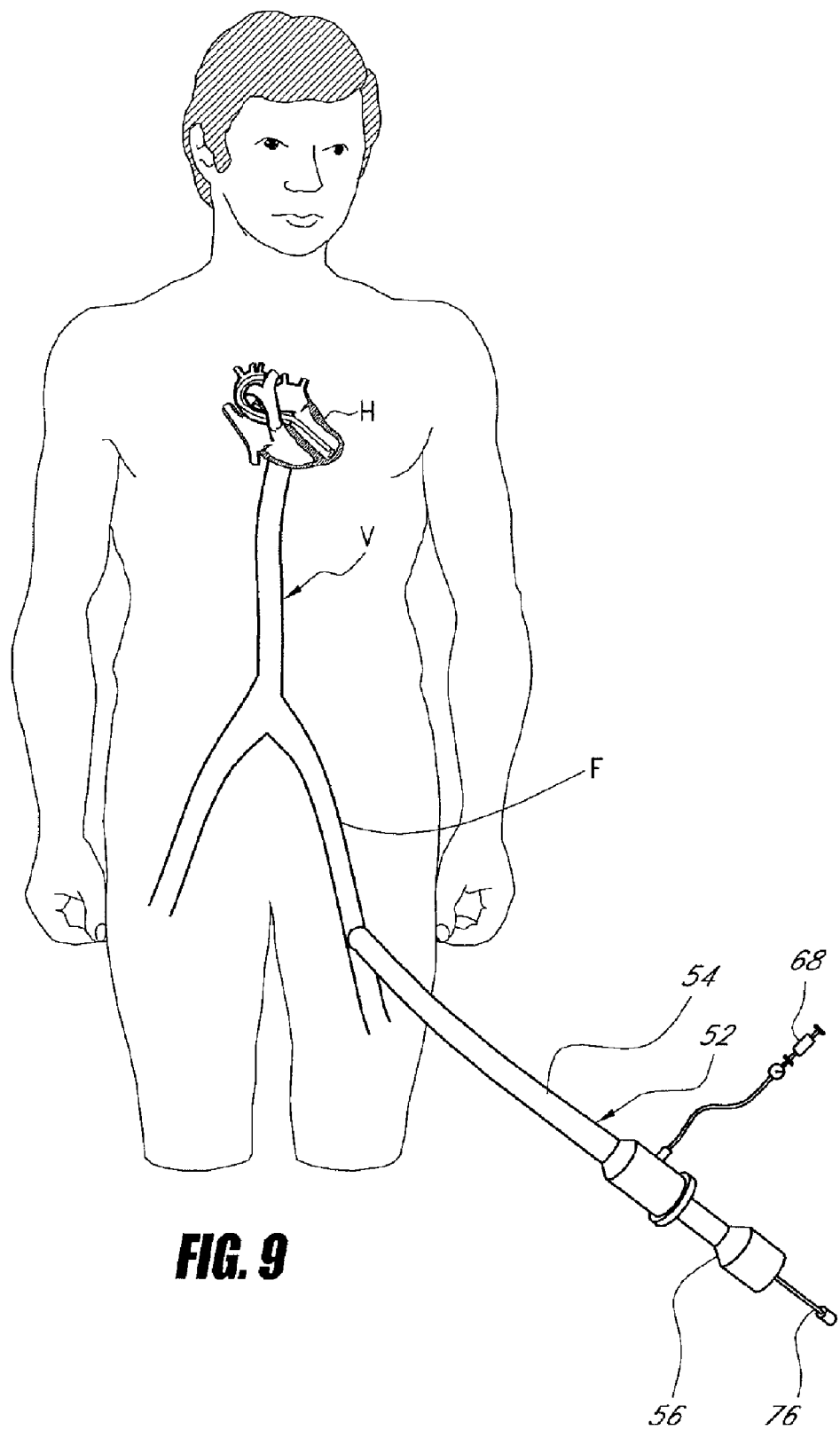
FIG. 9 is a schematic illustration of the system being used to remodel a left ventricle of a patient's heart and being introduced into the patient's vasculature through the femoral artery.

Preferred embodiments and methods of the present tissue remodeling system permit remodeling, tissue joining, or tying of soft tissue and, in certain preferred arrangements, permit a remodeling of the left ventricle of a heart to reduce the volume of the ventricle. Preferably, the preferred embodiments permit soft tissue remodeling while avoiding the disadvantages of more invasive procedures and the complications that may occur as a result of such procedures. The preferred embodiments and methods may also permit tissue remodeling in patients that are otherwise unable to undergo conventional surgical procedures, such as open heart surgery. Preferred embodiments of the present system permit the duplication of the results of surgical procedures in reducing the volume of the left ventricle by a percutaneous transvascular technique using catheter-based devices. In addition, the preferred embodiments and method disclosed herein may be modified or adapted for use in the remodeling of soft tissue other than the left ventricle of a patient's heart.

FIGS. 1-8 illustrate a first preferred embodiment of a tissue remodeling system, generally referred to by the reference numeral 50. The illustrated system 50 includes a catheter assembly 52, which preferably includes multiple catheters, or catheter bodies. For simplicity, both the catheter assembly 52 and individual catheter bodies may be referred to by the term "catheter." Preferably, the catheter 52 is sized, shaped and otherwise configured to be movable within a patient's vasculature to a desired remodeling site from a desired insertion site, such as the femoral artery, for example.

Thus, the catheter 52 may be constructed from a variety of suitable materials using a variety of suitable fabrication techniques, such as those commonly known and used in constructing catheters for medical use. For example, the catheter 52, and other catheters discussed herein, may be constructed from polyethylene, polyurethane, silicone or polytetraflouroethylene, or other suitable materials by any suitable process. The illustrated catheter 52 includes a pair of coaxial catheter bodies. The outer catheter body 54 is referred to as a guide catheter, or access catheter, herein. The illustrated access catheter 54 may have an outer diameter of about 26F (French) and an inner (lumen) diameter of about 22F. However, other suitable dimensions may be selected to suit an individual application of the catheter 54.

The inner catheter 56 is movable within the access catheter 54 and is referred to as a tissue-penetrating catheter herein. The inner catheter 56, in the illustrated arrangement, preferably has an outer diameter of about 18F and an inner (lumen) diameter of about 13F. However, other dimensions may be selected to suit a desired application of the catheter 56.

In the illustrated arrangement, the access catheter 54 is configured to be steerable to permit the access catheter 54 to be guided through vasculature to a desired site. Preferably, an anchoring ring 58 is embedded within a distal end 54a of the access catheter 54. A deflection wire 60 preferably is connected to and extends from the anchor ring 58 within a wall of the catheter 54 to a proximal end of the catheter 54 where it is connected to a control knob 62. Thus, the control knob 62 permits a user to selectively move the deflection wire 60 relative to the catheter 54 to deflect a distal end 54a of the access catheter 54. Deflection of the distal end 54a of the access catheter 54 assists a user to routing the catheter 54 through the vasculature of a patient in a desired path. Alternatively, other suitable steering arrangements or positioning methods of the access catheter 54 may be employed. In one arrangement, the access catheter 54 may be configured to slide over a previously placed guidewire (not shown).

Preferably, the distal end 54a of the access catheter 54 is configured to be atraumatic to the patient and, in particular, to the tissue at or near the remodeling site. In the illustrated arrangement, the distal tip 54a of the access catheter 54 carries an inflatable, annular balloon 64. Preferably, the balloon 64 is normally carried by the access catheter 54 in an uninflated condition so as not to interfere with the passage of the catheter 54 through a patient's vasculature. Once in place within the left ventricle, the balloon 64 may be inflated to contact the ventricle wall, help stabilize the distal end of the access catheter 54 and inhibit a distal tip 54a of the access catheter 54 from damaging tissue. Preferably, the balloon 64, in an inflated condition, extends beyond an end surface of the distal end 54a to inhibit the distal end surface from contacting the wall of the heart. The balloon 64 may be constructed from a suitable, material and mounted to the access catheter 54 by any suitable technique.

An inflation passage 66 is defined within a wall of the access catheter 54 and communicates with an interior space of the balloon 64. A proximal end of the inflation passage 66 extends from a proximal end 54b of the access catheter 54, preferably on a handle defined by the proximal end 54b and near the steering knob 62. Thus, the inflation passage 66 may be connected to a suitable fluid supply source 68, which is configured to supply a pressurized fluid to the balloon 64 through the inflation passage 66. In the illustrated arrangement, the source of fluid 68 is a standard syringe that is connected to the inflation passage 66 preferably by suitable plastic tubing 70. Any type of suitable connector, such as a luer lock for example, may be used to interconnect the tubing 70 with the access catheter 54 and the source of fluid 68. If desired, a pressure indicator 72 may be provided within the system to provide an indication of the fluid pressure within the balloon.

As described above, the tissue-penetrating catheter 56 is movable within the access catheter 54. Preferably, the tissue-penetrating catheter 56 is movable to a stowed position within the access catheter 54 wherein, preferably, the entire distal end 56a of the tissue-penetrating catheter 56 is positioned within the distal end 54a of the access catheter 54. Preferably, the tissue-penetrating catheter 56 is also movable to a protruding position relative to the access catheter 54 wherein the distal end 56a of the tissue-penetrating catheter 56 is exposed from the distal end 54a of the access catheter 54. Preferably, a proximal end 56b of the tissue-penetrating catheter 56 defines a handle configured to permit a user to move the tissue-penetrating catheter 56 between its stowed and protruding positions.

In the illustrated arrangement, the distal end 56a of the tissue-penetrating catheter 56 is configured to create a passage within soft tissue of a patient and deliver an implant, or a tissue remodeling clip 74, into the passage. With reference to FIGS. 1 and 4, preferably the tissue-penetrating catheter 56 carries the tissue remodeling clip 74 within its distal end 56a. In the illustrated arrangement, a push rod 76 is positioned within the tissue-penetrating catheter 56 and proximal of the clip 74. The distal end 76b of the push rod 76 preferably defines a contact surface configured to permit the push rod 76 to apply a force to the clip 74. A proximal end 76b of the push rod 76 terminates in a handle, which permits a user of the system 50 to deploy the clip 74 from the tissue-penetrating catheter 56 by advancing the push rod 76 within the tissue-penetrating catheter 56.

Desirably, the distal end 56a of the tissue-penetrating catheter 56 assumes a nonlinear shape in a relaxed position. That is, preferably, when no restraining force is present on the distal end 56a of the tissue-penetrating catheter 56, the distal end 56a moves into a nonlinear orientation. Preferably, in a relaxed position, the distal end 56a is arcuate or curved and, more preferably, assumes a generally helical shape. The helix angle, radius and length of the distal end 56a may be altered to suit the properties of the tissue that to be remodeled. Preferably, at least the distal end 56a of the tissue-penetrating catheter 56 preferably is constructed from a suitable shape memory material that is configured to have a desired shape in its relaxed position, such as a nickel titanium alloy (NiTi), for example.

With such an arrangement, when the tissue-penetrating catheter 56 is in its stowed position, the access catheter 54 constrains the distal end 56a into a generally straightened orientation, or a shape that generally matches the shape of the distal end 54a of the access catheter 54 at a given time. However, when the tissue-penetrating catheter 56 is moved to its protruding position, the distal end 56a tends to move toward its predefined relaxed shape. In use, outside forces may inhibit the distal end 56a of the tissue-penetrating catheter 56 from reaching its full relaxed orientation, such as forces imposed by the tissue in which the distal end 56a is penetrating. Preferably, the relaxed shape of the distal end 56a of the tissue-penetrating catheter 56 is configured such that the shape assumed by the distal end 56a will be generally as desired in the presence of anticipated restraining forces, such as those originating from soft tissue of a patient, for example. Furthermore, although a helical shape is preferred, in other applications other shapes may be desirable, as will be appreciated by one of skill in the art. Preferably, the tip of the distal end 56a of the tissue-penetrating catheter is angled relative to a longitudinal axis of the catheter 56 to permit the distal end 56a of the tissue-penetrating catheter 56 to pierce soft tissue. Other suitable tip shapes that would permit the catheter 56 to pierce or penetrate soft tissue may also be used.

Preferably, the tissue remodeling clip 74 is configured to be movable between a nonlinear, relaxed position and a biased, or straightened position. Thus, the clip 74 preferably is constructed from a shape memory material, such as NiTi. When stowed within the tissue-penetrating catheter 56, preferably the clip 74 is biased into a generally linear orientation or a shape that generally matches the shape of the distal end 56a of the tissue-penetrating catheter 56. When deployed from the tissue-penetrating catheter 56, the clip 74 moves toward its relaxed position wherein, preferably, a first end 74a of the clip 74 is resiliently biased to move toward a second end 74b, as illustrated in FIG. 6a. In the illustrated arrangement, the clip 74 in a relaxed position assumes a generally circular shape. However, the clip 74 may be configured to assume other suitable shapes in its relaxed position.

The illustrated clip 74 may have a diameter from between about 0.005 inches to about 0.05 inches. The circular loop defined by the clip 74 in its relaxed position may have a diameter from about 0.06 inches to about 0.5 inches. A length of the clip 74 may be from about 0.5 inches to about 2 inches. These dimensions are presently preferred for a clip 74 configured to remodel the left ventricle of a patient's heart. In other applications, other dimensions may be desirable. The clip 74 may be shaped by winding a work piece on a mandrel and then exposing the work piece to a heat cycle of about 500 degrees centigrade for a period of between about 10 minutes to about 60 minutes, depending on the strength, spring rate and oxide layer desired. Furthermore, other suitable methods of shaping the clip 74 may also be used.

As illustrated in FIG. 6c, when implanted into soft tissue T, the clip 74 moves toward its relaxed position such that the first end 74a applies a force to the tissue T at a first location and the second end 74b applies a force to the tissue T at a second location spaced from the first location to remodel the soft tissue T. As discussed above with respect to the distal end 56a of the tissue-penetrating catheter 56, in use the clip 74 may not move completely to its relaxed position due to restraining forces, such as forces imposed by the soft tissue. Thus, the tissue remodeling position of the clip 74 may fall somewhere between its straightened position and its relaxed position. Furthermore, the ends 74a, 74b of the clip 74 may remain embedded within the soft tissue T. However, preferably the clip 74 does not protrude through an external surface of the tissue wall (the non-entry side of the wall). That is, when the clip 74 is implanted within a ventricle of a heart, preferably, the clip 74 enters the heart wall from a location internal the ventricle and does not pass through an outer surface of the heart wall.

FIGS. 7a-7d illustrate a modification of the tissue remodeling clip 74 and is generally referred to by the reference numeral 80. The clip 80 includes a pledget at each of its first and second ends 80a, 80b. The pledgets 82 preferably are relatively thin, circular members which have a diameter substantially larger than a diameter of the clip 80 when the pledgets 82 are in an expanded position (FIGS. 7a, 7b and 7d). Therefore, the pledgets 82 inhibit the ends 80a, 80b of the clip 80, once passed completely through soft tissue T, from pulling back through the surface of the tissue T. Thus, the ends 80a, 80b of the clip 80 preferably remain exposed from the tissue T. Preferably, the pledgets 82 are collapsible to permit the clip 80 to be initially implanted into the tissue T, as illustrated in FIG. 7c.

In a preferred embodiment, the pledgets 82 may be constructed from a piece of polymer material, such as Dacron, that is cut into a circular shape with a central aperture. The pledgets 82 may be placed over the ends 80a, 80b of the clip 80 and the ends 80a, 80b enlarged to retain the pledgets 82 on the clip 80. The enlarged ends may be formed by resistance spot welding, laser welding, or other suitable methods. Further, the enlarged ends may be created by additional members that are separate from, and secured to, the clip 80.

Another modification of the clip 74 of FIG. 6 is illustrated in FIGS. 8a-8c and is referred to by the reference numeral 90. The clip 90 of FIGS. 8a-8c includes a plurality of barbs 92 on each of the first and second ends 90a, 90b. The barbs 92 are configured to penetrate tissue to inhibit movement of the clip 90 relative to the tissue. The barbs 92 (and ends 90a, 90b) may be embedded in the tissue T when the clip 90 is implanted, as shown in FIG. 8c, or, alternatively, may be exposed from the tissue T. The barbs 92 may be created by a laser cutting technique, electrical discharge machining (EDM), mechanical cutting techniques, or other suitable processes. In addition, other suitable stabilizing members or arrangements to inhibit movement of the clips 74, 80, 90 relative to the tissue into which they are implanted may also be used. Furthermore, although the illustrated clips 74, 80, 90 are circular in cross-sectional shape, other suitable shapes may also be used, such as a rectangular or elliptical cross-section, for example.

FIGS. 9-12 illustrate a preferred method for utilizing the system 50 of FIGS. 1-8 to remodel soft tissue of a patient P and, preferably, to remodel the left ventricle of the patient's P heart H. In a preferred application of the method illustrated in FIGS. 9-12, access to the left ventricle of the heart H is achieved through the patient's vasculature V from an insertion site in the femoral artery F. If desired, a sleeve (not shown) may be inserted into the femoral artery F to provide access for the catheter 52. Alternatively, other methods of accessing the left ventricle, preferably using a percutaneous approach, may also be used.

Figure 10:
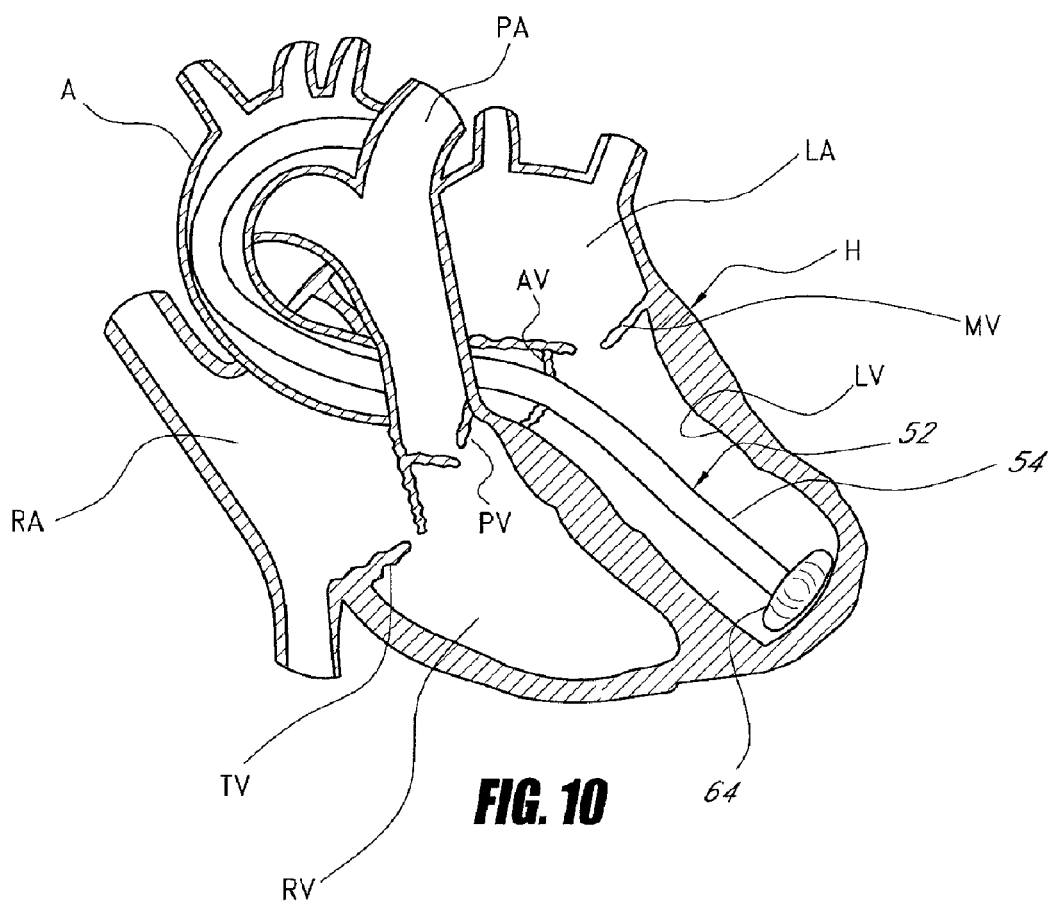
FIG. 10 is a cross-sectional view of the patient's heart with the catheter within the left ventricle and the balloon in an inflated position.

With reference to FIG. 10, the catheter 52 is illustrated accessing the left ventricle LV of the patient's heart through the aorta A. The catheter 52 may be routed to the left ventricle LV by any suitable method. For example, as described above, the catheter 52 may be steerable to permit a user to navigate the patient's P vasculature using a suitable imaging technique. For example, preferably, the method is performed by a cardiologist in a cathlab setting using a transesophageal echocardiogram (TEE) or angiographic fluoroscopy imaging technique to accomplish each of the steps described herein that take place within the patient P. In addition, other imaging techniques may also be used. If desired, a guide wire (not shown) may be routed to the left ventricle LV and the catheter 52 may be introduced to the left ventricle LV over the guide wire.

As will be appreciated by one of skill in the art, a human heart H includes a right atrium RA, a left atrium LA, a right ventricle RV and a left ventricle LV. The tricuspid valve TV separates the right atrium from the right ventricle and the pulmonary valve PV separates the right ventricle from the pulmonary artery PA. The mitral valve MV separates the left atrium LA from the left ventricle LV and they aortic valve AV separates the left ventricle LV from the aorta A.

As illustrated in FIG. 10, in the preferred method, the balloon 64 is inflated so that the catheter assembly 52, and access catheter 54 in particular, may be held against the wall of the left ventricle LV without causing damage thereto. Thus, preferably the balloon 64 supports a distal tip of the access catheter 54 at least slightly spaced from the wall of the left ventricle LV. The balloon 64 may also contact the wall of the left ventricle LV adjacent the desired remodeling site to inhibit the distal end 54a of the access catheter 54 from moving once it is positioned.

Figure 11A:
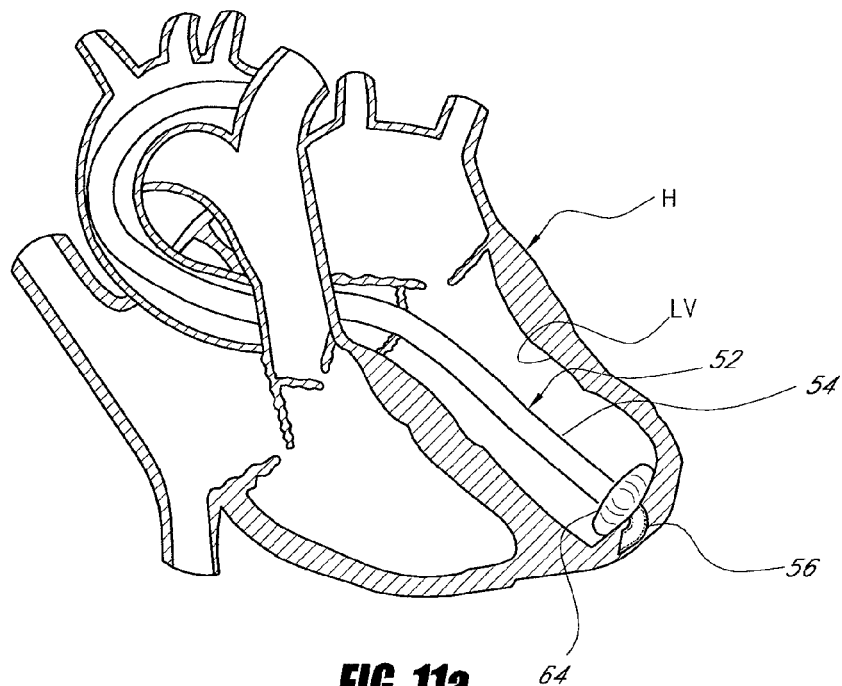
FIG. 11a is a cross-sectional view of the patient's heart with the catheter in contact with a wall of the left ventricle and the tissue-penetrating catheter penetrating the wall of the left ventricle.

With reference to FIG. 11a, once the access catheter 54 is guided to a desired position within the left ventricle LV, the tissue penetrating catheter 56 may be moved from its stowed position within the access catheter 54 towards its protruding position such that the tissue-penetrating catheter 56 creates a passage within the wall of the left ventricle LV. Preferably, the tissue-penetrating catheter 56 creates a passage that has a shape generally corresponding to the relaxed shape of the distal end 56a of the tissue-penetrating catheter 56. If desired, one or both of the access catheter 54 and the tissue-penetrating catheter 56 may be rotated to assist the tissue-penetrating catheter 56 in creating a passage within the wall of the left ventricle, as illustrated by the arrows 94 in FIG. 11b.

Figure 11B:
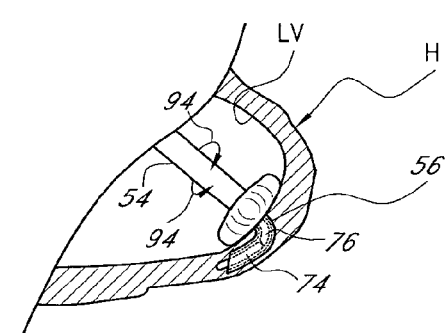
FIG. 11b is an enlarged view of a distal end portion of catheter with the tissue-penetrating catheter being rotated about is longitudinal axis to create a generally helical passage within the wall of the left ventricle.
Figure 11C:
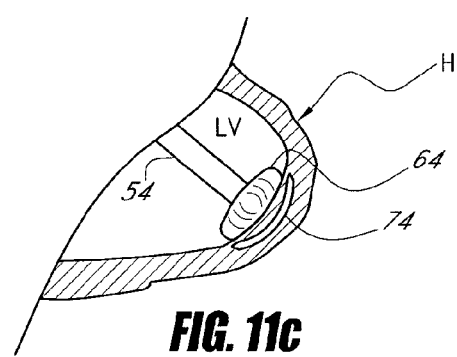
FIG. 11c is an enlarged view of the heart with the clip implanted into the passage created by the tissue-penetrating catheter.
Figure 11D:
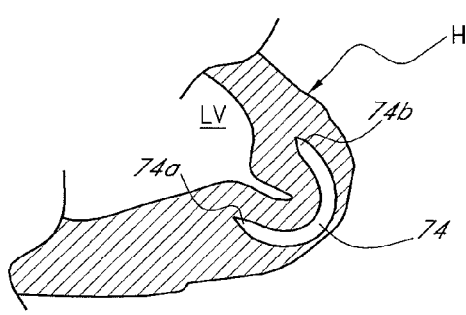
FIG. 11d is an enlarged view of the heart with the clip in a tissue remodeling position.

With reference to FIG. 11c, once the passage has been created within the wall of the left ventricle LV, the push rod 76 may be used to hold the clip 74 in position while permitting the tissue-penetrating catheter 56 to be withdrawn from the passage and into the access catheter 54, thus leaving the clip 74 in place within the passage in the wall of the left ventricle LV. Alternatively, the tissue-penetrating catheter 56 may be withdrawn from the passage, along with the clip 74, and the push rod 76 used to subsequently deploy the clip 74 into the preformed passage. The preferred method of deploying the clip 74 may depend on individual user preference, the shape of the clip 74 or the properties of the soft tissue T, among other considerations.

As illustrated in FIG. 11c, with the distal end of the access catheter 54 and balloon 64 pressed against the wall of the left ventricle LV, the clip 74 is inhibited from moving substantially toward its relaxed position. With reference to Figure lid, once the access catheter 54 is pulled away from the wall of the left ventricle LV, the tissue remodeling clip 74 may move substantially toward its relaxed position, thus bringing the ends 74a, 74b of the clip 74 toward one another to draw the portions of the ventricle wall associated with each end 74a, 74b toward one another. Accordingly, the implantation of the clip 74 thereby remodels and preferably reduces the volume of the left ventricle LV. In the illustrated arrangement, the clip 74 is implanted in the free wall of the left ventricle LV. That is, the clip 74 is implanted into tissue defining a wall of the ventricle other than the septal wall. However, in some applications it may be desirable to remodel the septal wall, such as when performing a septal defect repair. Thus, the present systems disclosed herein may be used to remodel the septal wall, or may be appropriately modified to remodel the septal wall, if so desired.

With reference to FIG. 11c, once the passage has been created within the wall of the left ventricle LV, the push rod 76 may be used to hold the clip 74 in position while permitting the tissue-penetrating catheter 56 to be withdrawn from the passage and into the access catheter 54, thus leaving the clip 74 in place within the passage in the wall of the left ventricle LV. Alternatively, the tissue-penetrating catheter 56 may be withdrawn from the passage, along with the clip 74, and the push rod 76 used to subsequently deploy the clip 74 into the preformed passage. The preferred method of deploying the clip 74 may depend on individual user preference, the shape of the clip 74 or the properties of the soft tissue T, among other considerations.

Figure 12:
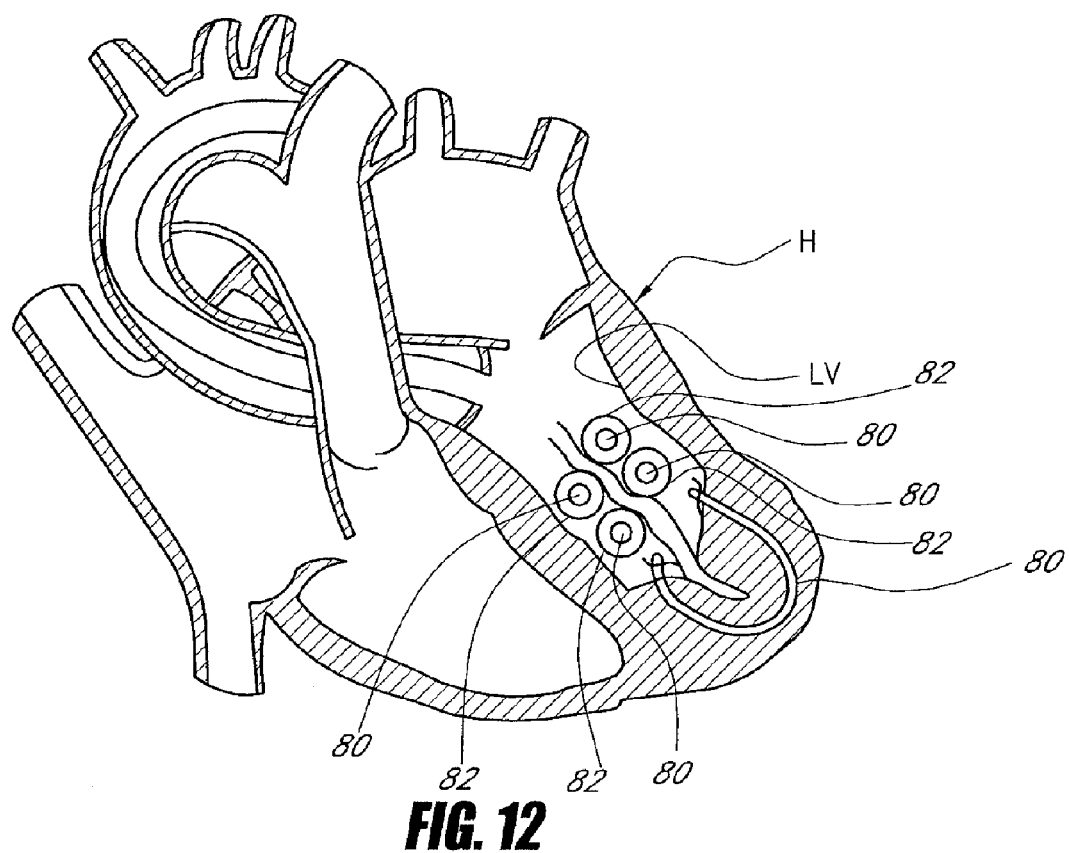
FIG. 12 is a cross-sectional view of the heart illustrating several tissue remodeling clips positioned within the left ventricle.
Figure 13:
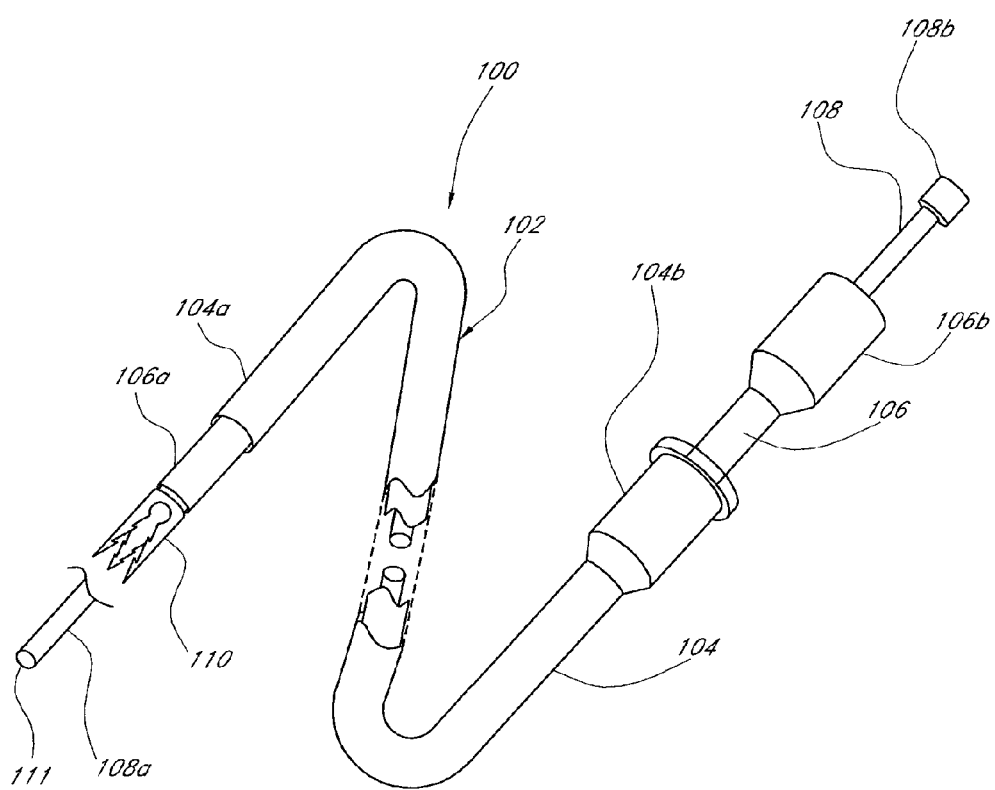
FIG. 13 is perspective view of a modification of the tissue remodeling system of FIG. 1 and includes a catheter configured to deploy a collapsible tissue anchor.

FIG. 12 illustrates a plurality of remodeling clips 80 implanted within the wall of the left ventricle to remodel the left ventricle LV and, preferably, reduce the volume of the left ventricle LV. In some applications, only one clip 74, 80, 90 may be desired and, in other applications, a plurality of clips 74, 80, 90 may be used depending on what level of remodeling, or reduction in volume, is desired. In a preferred method, enough clips 74, 80, 90 are implanted to substantially completely fold away the akinetic portion of the ventricle tissue. However, it is contemplated that one of skill in the art will be able to determine a suitable number of clips 74, 80, 90 to be implanted depending on a particular application, the level of remodeling desired, the properties of the clip 74, 80, 90, and the properties of the soft tissue, among other considerations.

FIGS. 13-17 illustrate a second embodiment of a tissue remodeling system, generally referred to by the reference numeral 100. Preferably, the system 100 is a catheter-based tissue remodeling system that is configured to facilitate the remodeling of soft tissue of a patient at a desired site that is accessed through the patient's vasculature. The illustrated system 100 is configured to remodel a patient's heart and, preferably, reduce the volume of the left ventricle of the heart. However, as described above, the systems and methods disclosed herein may be used to otherwise manipulate, gather, fold, tie or join soft tissue, such as to achieve a closing of a tissue cavity, for example.

The system 100 includes a catheter assembly 102 including a plurality of coaxial catheter bodies. In the illustrated arrangement, the catheter assembly 102 includes a guide catheter, or access catheter 104. A delivery catheter 106 is movable within a lumen of the access catheter 104. Preferably, a guide wire 108 is movable within a lumen of the delivery catheter 106. The catheter 102 is configured to deliver an implant, or collapsible tissue anchor 110, to a desired tissue remodeling site, such as the left ventricle of the heart in the illustrated arrangement, for example.

Preferably, the access catheter 104 is substantially similar to the access catheter 54 of the system 50 of FIGS. 1-8. The access catheter 104 includes a distal end 104a configured to be introduced into the left ventricle of a patient's heart and a proximal end 104b defining a handle. The access catheter 104 may be of any suitable size, shape, and length to extend from the desired remodeling site to a site external the patient through a suitable route. For example, the illustrated catheter 102 preferably is sized to extend from a left ventricle of a patient's heart to an external site adjacent the patient's femoral artery. Preferably, the access catheter 104 may have an outer diameter of about 26F and an inner (lumen) diameter of about 23F. However, other suitable dimensions may be used to suit a desired application. Furthermore, the catheter 102 may be constructed of any suitable material for use in a medical catheter application, as described above.

The delivery catheter 106 is configured to be axially movable within the access catheter 104. The delivery catheter 106 includes a distal end 106a, which is configured to support the tissue anchor 110, and a proximal end 106b defining a handle. The delivery catheter 106 may be constructed from any suitable material, as described above, and preferably has an outer diameter of about 0.25 inches and an inner (lumen) diameter of about 0.125 inches. However, the dimensions may be adjusted to suit a desired application.

The guide wire 108 preferably is configured to be deliverable through the vasculature of a patient to the left ventricle as an individual component to permit the access catheter 104 and delivery catheter 106 to be introduced into the left ventricle by being passed over the previously placed guide wire 108. Preferably, the guide wire 108 includes a tip 111 at its distal end 108a that is configured to be atraumatic to tissue that it comes into contact with. Desirably, the guide wire 108 also includes a proximal end 108b, which defines a handle or other structure that permits a user to manipulate the guide wire 108.

Figure 14:
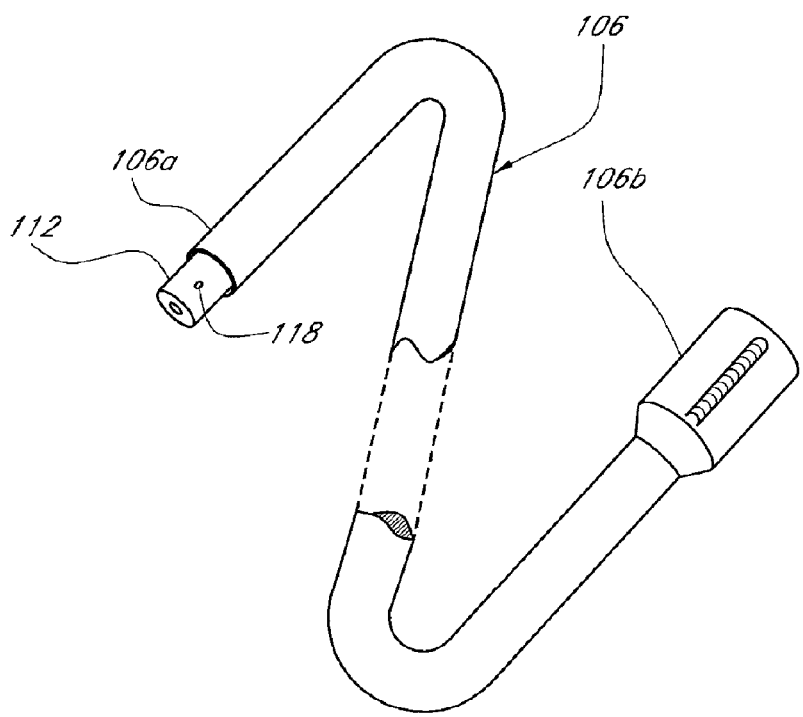
FIG. 14 is a perspective view of a tissue anchor delivery catheter body of the system of FIG. 13.
Figure 15:
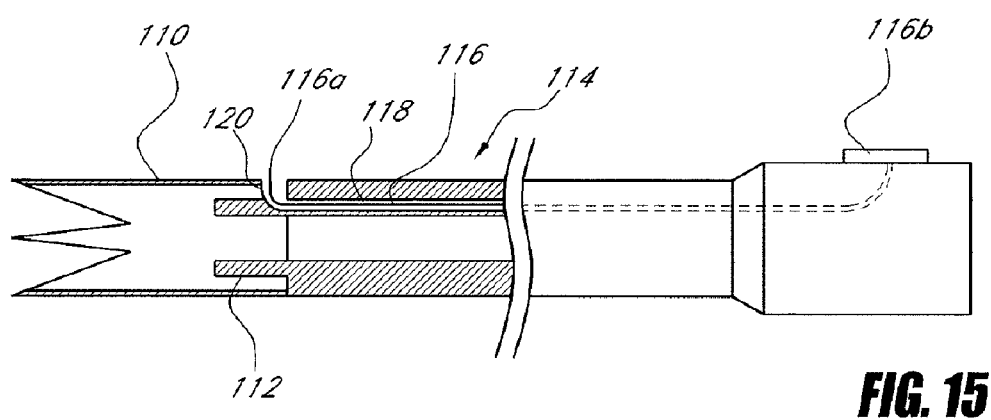
FIG. 15 is a partial cross-sectional view of the tissue anchor delivery catheter of FIG. 14.

With reference to FIGS. 14 and 15, desirably, the delivery catheter 106 includes a docking tip 112 at its distal end 106a. Preferably, the tip 112 defines an outer surface that has a reduced diameter relative to a diameter of the outer surface of the remainder of the delivery catheter 106. The docking tip 112 is sized and shaped to support a proximal end of the tissue anchor 110 thereon. Thus, preferably, an outer diameter of the tissue anchor 110 is generally equal to an outer diameter of the delivery catheter 106 such that when the tissue anchor 110 is positioned on the tip 112, the transition between the catheter 106 and the tissue anchor 110 is relatively seamless. Although the collapsible tissue anchor 110 is illustrated as surrounding the docking tip 112 in the illustrated arrangement, other suitable arrangements to interconnect the tissue anchor 110 and the delivery catheter 106 may also be employed.

Preferably, the delivery catheter 106 includes a retention mechanism 114 that is configured to secure the tissue anchor 110 to the distal end 106a of the delivery catheter 106 and selectively release the tissue anchor 110 from the delivery catheter 106. In the illustrated arrangement, a retention wire 116 is slidably received within a passage 118 defined by a wall of the delivery catheter 106. A distal end 116a of the retention wire 116 is configured to extend radially outwardly relative to the catheter 106, from the passage 118, into an aperture 120 of the tissue anchor 110. A proximal end 116b of the retention wire 116 includes a handle, or other suitable structure, which permits a user to retract the retention wire 116 within the passage 118 to release the tissue anchor 110 from the delivery catheter 106.

Alternatively, other suitable arrangements to retain and selectively release the tissue anchor 110 may also be employed. In some arrangements, for example, the tissue anchor 110 and catheter 106 may cooperate through a snap-fit arrangement in which an interference surface of the catheter 106 contacts an interference surface of the tissue anchor 110 to inhibit the anchor 110 from unintentionally becoming separated from the catheter 106. In such an arrangement, once the tissue anchor 110 is implanted within soft tissue, the anchor 110 may be automatically separated from the catheter 106 when a pulling force is applied to the catheter 106, as the tissue anchor 110 preferably will remain in place within the tissue.

FIGS. 16a and 16b illustrate the tissue anchor 110 removed from the delivery catheter 106. Preferably, the tissue anchor 110 includes a base portion 130 and a plurality of legs 132 which extend from the base portion 130. Desirably, the tissue anchor 110 includes between about 2 and 8 legs 132 and, preferably, between about 3 to 5 legs 132. The illustrated tissue anchor 110 includes three legs 132. However, other suitable numbers of legs 132 may be provided in accordance with the requirements an individual application.

Preferably, the tissue anchor 110 is a hollow member having a relatively thin wall thickness dimension. Preferably, the tissue anchor 110 is constructed of a metal material and, more preferably, from a shape memory material, such as NiTi, for example. Desirably, the base 130 is generally cylindrical in shape and the legs 132, preferably, are unitary with the base 130 and extend from the wall thereof. The base 130 may have an outer diameter of about 0.25 inches and an inside diameter of about 0.188 inches, for an anchor 110 configured to be implanted into a left ventricle of a patient's heart. However, the dimensions may be altered to achieve desired properties of the anchor 110 to suit an individual application, such as the closure of a cavity or hole, for example. The legs 132 may be created by cutting away material from an initial work piece, or sleeve, using a laser cutting method, or other suitable fabrication method.

Preferably, the legs 132 are movable, or flexible, relative to the base 130 between a relaxed position, wherein the legs 132 extend radially outward from the base 130, to a collapsed position, or tissue-remodeling position, wherein the legs 132 are biased inwardly from their relaxed position. Preferably, in the collapsed position, the legs 132 are generally aligned with the wall of the base 130. However, in some applications, the legs 132 may extend radially outward from the base 130, or radially inward from the base 130, in the tissue-remodeling position.

With reference to FIG. 17c, preferably, a retention member 134 is configured to retain the legs 132 in the tissue remodeling position. In the illustrated arrangement, the retention member 134 is in the form of a sleeve which slides over an outer surface of the legs 132, as is described in greater detail below. However, other suitable retention mechanisms may also be employed.

Each of the legs 132 preferably includes a pointed tissue piercing end 136 to permit the legs 132 to penetrate soft tissue of a patient, such as the wall of the left ventricle of the patient's heart. In addition, preferably the legs 132 include one or more barbs 138, which are configured to permit the legs 132 to enter soft tissue, in a first direction, and inhibit the legs 132 from being removed from the soft tissue in the opposite direction. Thus, once the legs 132 have penetrated the soft tissue, preferably, the tissue anchor 110 remains embedded in the tissue.

Desirably, the tissue anchor 110 is configured to inhibit the retention member 134 from inadvertently becoming dislodged from the tissue anchor 110. In the illustrated arrangement, the base 130 includes a plurality of pawls, or tabs 140, which are configured to permit the retention member 134 to move toward the distal end of the tissue anchor 110 and inhibit the retention member 134 from moving away from the distal end, toward the proximal end of the tissue anchor 110 past the tabs 140. Desirably, the tabs 140 are generally semicircular in shape and comprise an outwardly-bent portion of the material of the base 130 portion of the tissue anchor 110. Thus, the tabs 140 bend inwardly, into general alignment with the base 130, to permit the retention sleeve 134 to pass over. Once the retention sleeve 134 has passed over the tab 140, it returns to its outwardly-bent position to interfere with an attempt of the retention sleeve 134 in moving back over the tab 140, as illustrated in FIG. 17c. In some arrangements, tabs may also be defined by the legs 132. Furthermore, in an alternative arrangement, the tabs 140 may be defined by members that are separate from, and attached to, the tissue anchor 110.

In the illustrated arrangement, the base 130 includes several rows of tabs 140 wherein each row includes multiple tabs 140 arranged around the circumference of the base 130. In the illustrated arrangement, the tissue anchor 110 includes three rows of tabs 140, wherein each row includes three tabs 140 equally spaced about a circumference of the base 130. However, other suitable arrangements to permit unidirectional movement of the retention member 134 may also be used.

FIGS. 17a through 17c illustrate the tissue anchor 110 in several states of deployment from the catheter assembly 102. With reference to FIG. 17a, desirably the delivery catheter 106 is positioned within the access catheter 104 such that the tissue anchor 110 is substantially entirely enclosed within the access catheter 104 and constrained thereby into a collapsed position.

With reference to FIG. 17b, when the tissue anchor 110 is deployed from the access catheter 104, the legs 132 are permitted to move toward their relaxed position. It should be noted that the radial expansion of the legs 132 toward their relaxed position may be influenced by the distance of which the tissue anchor 110 is exposed from the access catheter 104. In some applications, legs 132 of the tissue anchor 110 may be completely deployed from the access catheter 104 prior to the legs 132 contacting soft tissue. Thus, in the absence of any other restraining force, the legs 132 would be in their fully relaxed position when contact with the soft tissue is made. In other applications, however, the legs 132 may be retained partially within the access catheter 104 so that the legs 132 are constrained from moving to their fully relaxed position. Accordingly, the diameter of a circle defined by the legs 132 (or the distance between the legs 132 and an axis of the catheter 104) may be altered as desired prior to contact with the soft tissue. In addition, other methods of facilitating the tissue anchor 110 in grabbing a portion of soft tissue of a desired size or shape may also be used.

With reference to FIG. 17c, the retention member, or locking sleeve 134, may be slid over the delivery catheter 106 and on to the tissue anchor 110 by a pusher catheter 142. The retention sleeve 134 may be pushed a sufficient distance on to the tissue anchor 110 to move the legs 132 toward a tissue remodeling position to achieve a desired amount of remodeling. Desirably, the tabs 140 inhibit the retention sleeve 134 from becoming disengaged with the tissue anchor 110. Alternatively, the legs 132 may be moved toward a tissue-remodeling position by another member and the retention sleeve 134 may be used simply to retain the legs 132 in the desired tissue-remodeling position.

FIGS. 18-22 illustrate a preferred method of remodeling soft tissue of a patient using the system 100 of FIGS. 13-17. The illustrated method utilizes the system 100 to remodel the left ventricle of a patient's heart and, preferably, to reduce the volume of the left ventricle. Desirably, access to the left ventricle is gained through the patient's vasculature beginning at an insertion site in the femoral artery F, as shown in FIG. 9. However, other methods of gaining access to the left ventricle may also be used.

Figure 18:
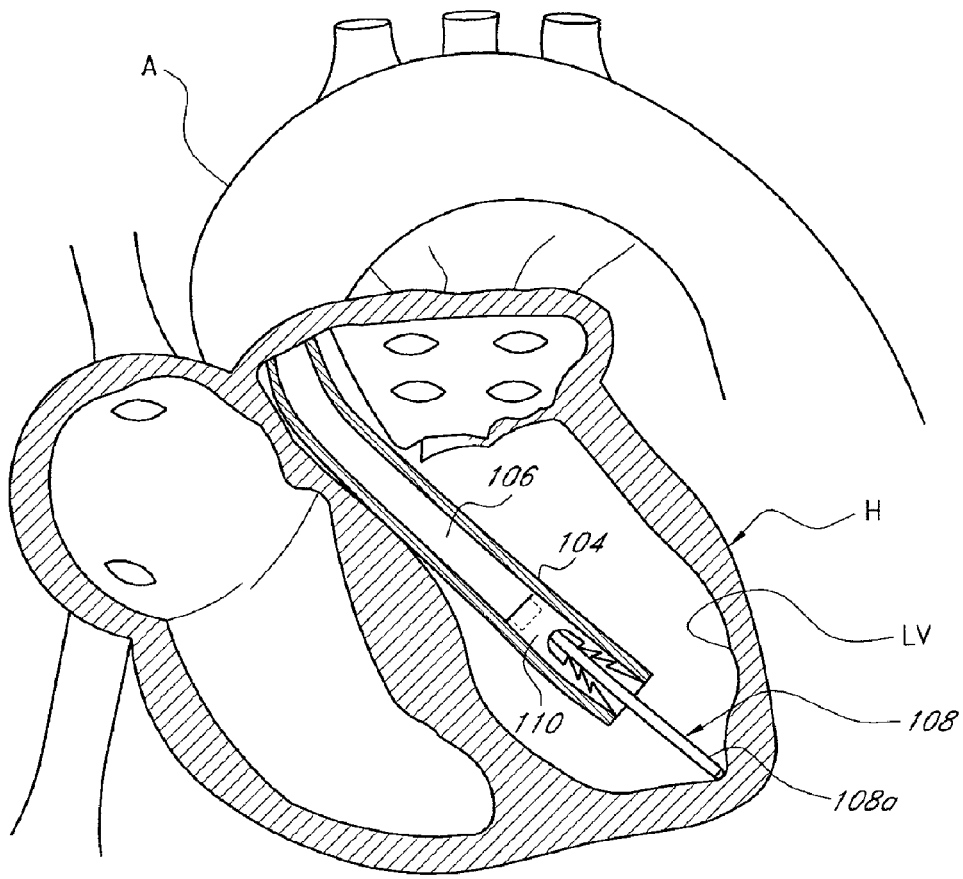
FIG. 18 is a cross-sectional view of a heart with the catheter inserted into the left ventricle.

With reference to FIG. 18, the guide wire 108 may be advanced through the patient's vasculature, from the femoral artery F, to enter the left ventricle LV through the aorta A using a suitable imaging technique, as described above. The guide wire 108 is positioned preferably such that its distal end 108a contacts a portion of the wall of the left ventricle LV where remodeling is desired. Subsequently, the delivery catheter 106 and access catheter 104 may be advanced over the guide wire 108, either individually or together, until the distal end of each approaches the wall of the left ventricle LV. Preferably, the distal end of the access catheter 104 and delivery catheter 106 are spaced from the wall of the left ventricle LV as illustrated in FIG. 18.

Figure 19:
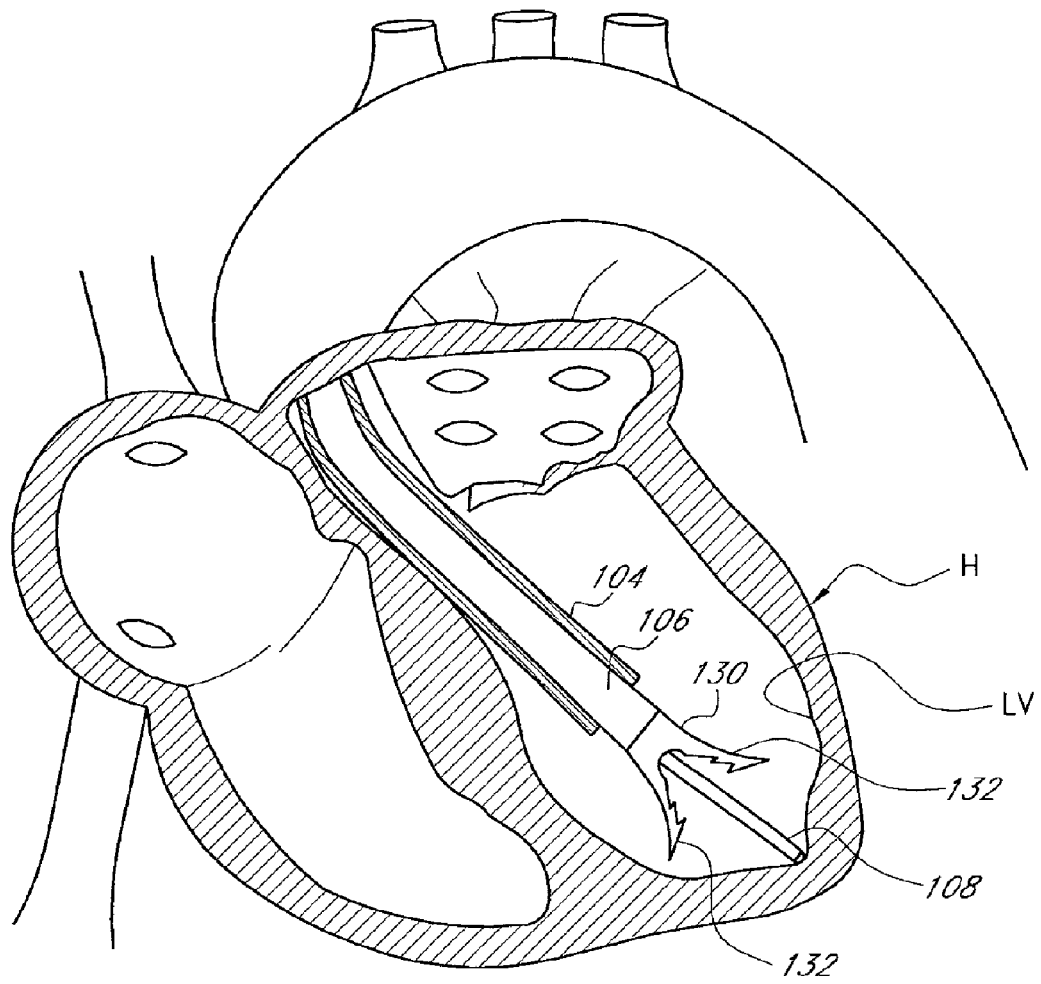
FIG. 19 is a cross-sectional view of the heart of FIG. 18 illustrating the tissue anchor deployed from a distal end of the delivery catheter.

With reference to FIG. 19, the delivery catheter 106 may be advanced relative to the access catheter 104 and guide wire 108 such that the tissue anchor 110 is deployed therefrom. Once the tissue anchor 110 is at least partially deployed from the access catheter 104, the legs 132 may move toward their relaxed, or radially outward position. As described above, the distance that the tissue anchor 110 is deployed from the access catheter 104, which preferably applies a restraining force to the legs 132, influences a distance that the legs 132 may expand from a center axis of the catheter 104. Such a technique may be used to determine the amount of tissue grasped by the legs 132 of the tissue anchor 110. In the illustrated arrangement, the tissue anchor 110 is shown completely deployed from the access catheter 104.

Figure 20:
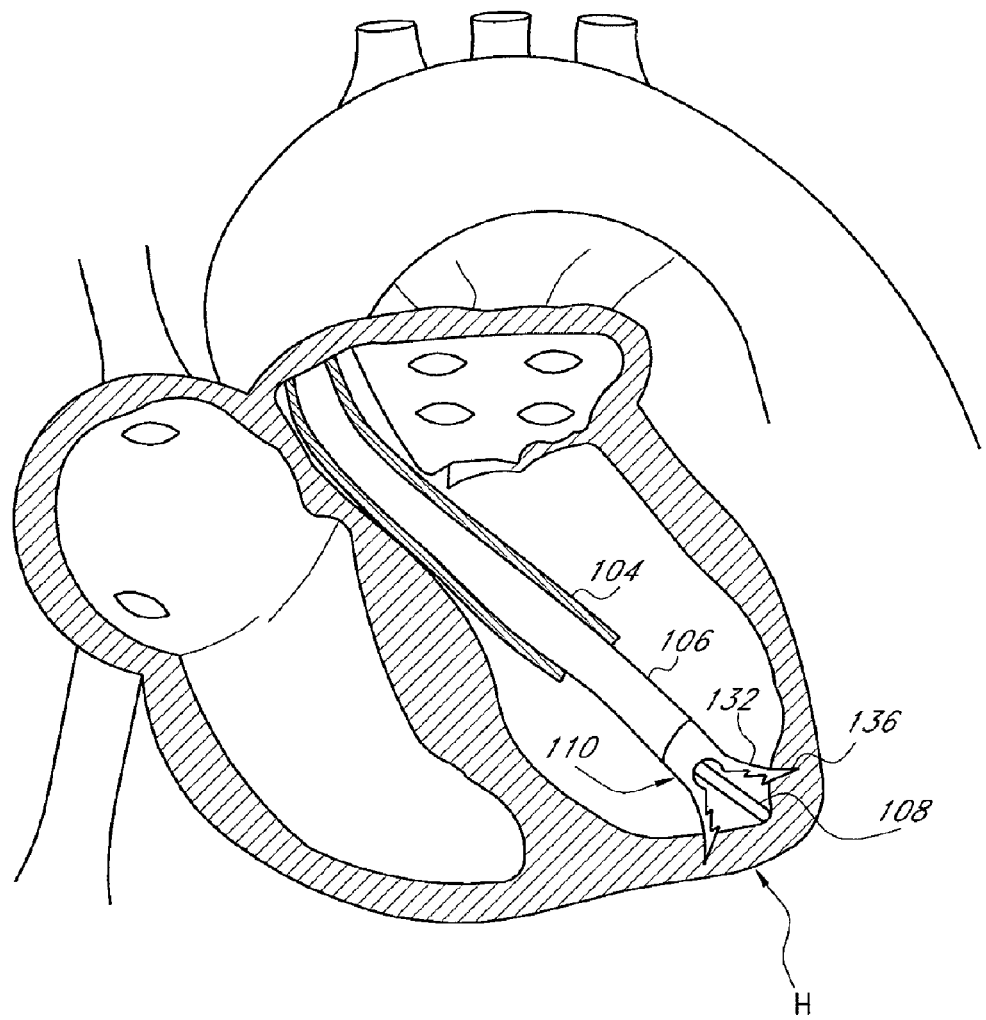
FIG. 20 is a cross-sectional view of the heart of FIG. 18 illustrating the tissue anchor penetrating the wall of the left ventricle.

With reference to FIG. 20, the delivery catheter 106 and, if desired, the access catheter 104, may be moved relative to the guide wire 108 toward the wall of the left ventricle LV until the tips 136 of the legs 132 of the tissue anchor 110 penetrate the wall of the left ventricle LV. Desirably, with the illustrated tissue anchor 110, the legs 132 do not penetrate an outer surface of the heart H. However, in some arrangements, it may be desirable that the legs 132 pass completely through the wall of the heart H. Once the legs 132 have been entered the wall of the left ventricle LV, the barbs 138 preferably inhibit the legs 132 from being removed therefrom.

Figure 21:
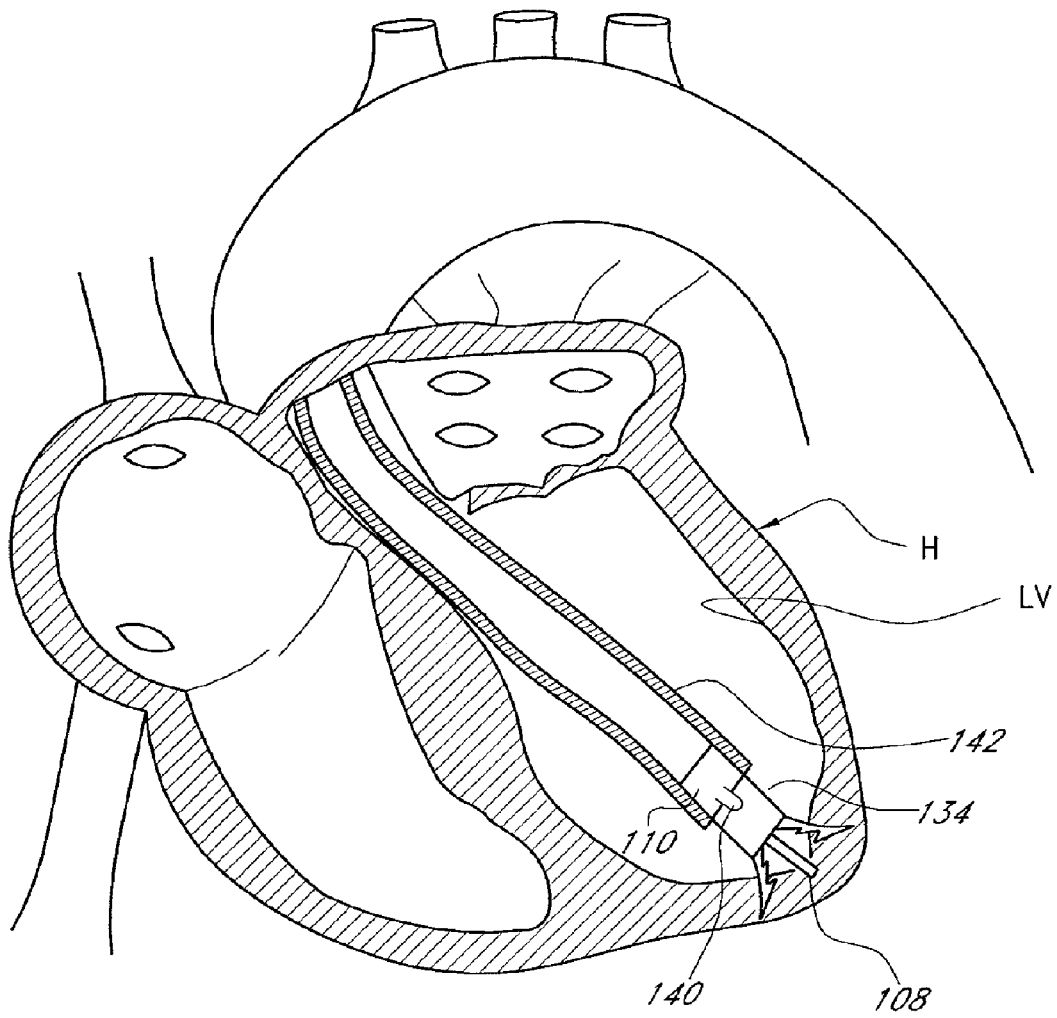
FIG. 21 is a cross-sectional view of the heart of FIG. 18 illustrating the retaining member retaining the tissue anchor in a tissue remodeling position.

With reference to FIG. 21, the access catheter 104 may be removed from the delivery catheter 106 to permit the locking clip 134 to be positioned over the delivery catheter 106. The pusher catheter 142 may then be used to move the locking ring 134 to the distal end of the delivery catheter and over the tissue anchor 110 to move the legs 132 toward their tissue-remodeling position. As described above, the locking sleeve 134 may be moved on to the tissue anchor 110 a sufficient distance to move the legs 132 until a desired level of remodeling is accomplished. The pusher catheter 142 may then be removed and the tabs 140 of the tissue anchor 110 inhibit the locking ring 134 from becoming disengaged with the tissue anchor 110 and thereby retain the tissue anchor 110 in its tissue remodeling position. Alternatively, the access catheter 104 may be adapted to carry and deploy the locking sleeve 134 to eliminate the need for a separate pusher catheter 142.

Figure 22:
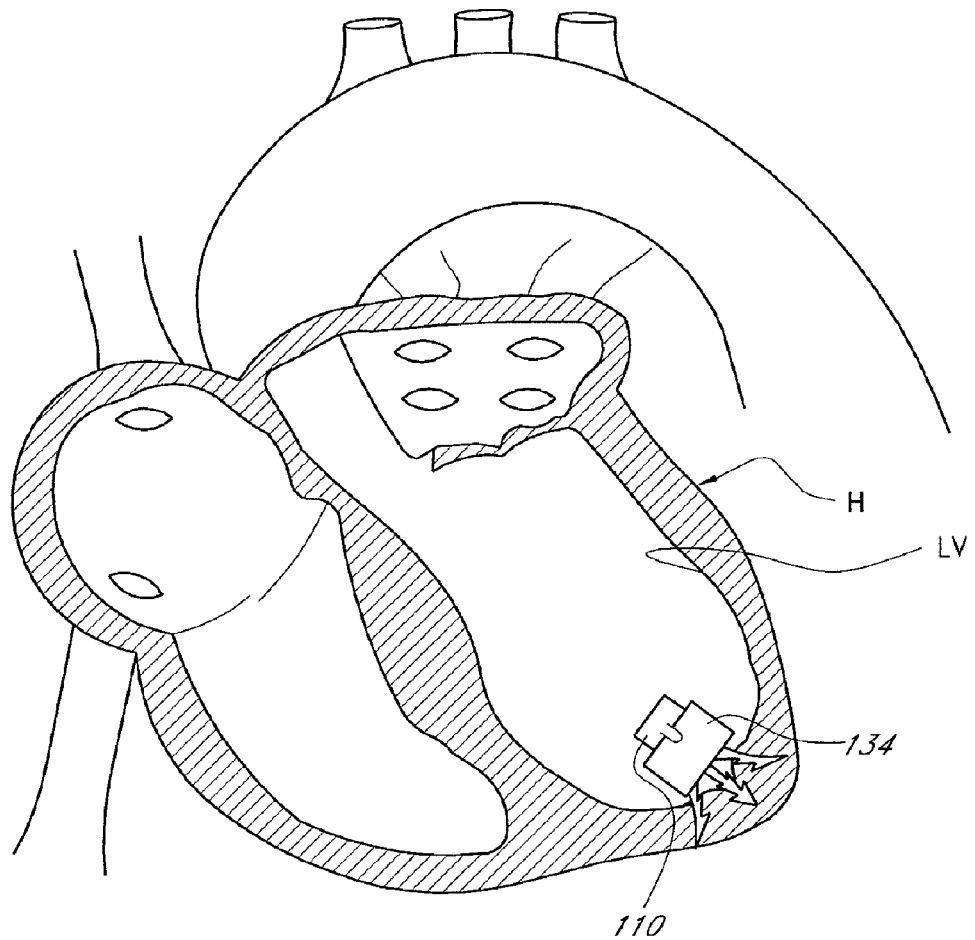
FIG. 22 is a cross-sectional view of the heart of FIG. 18 illustrating the tissue anchor released from the catheter and remodeling the wall of the left ventricle.
Figure 23:
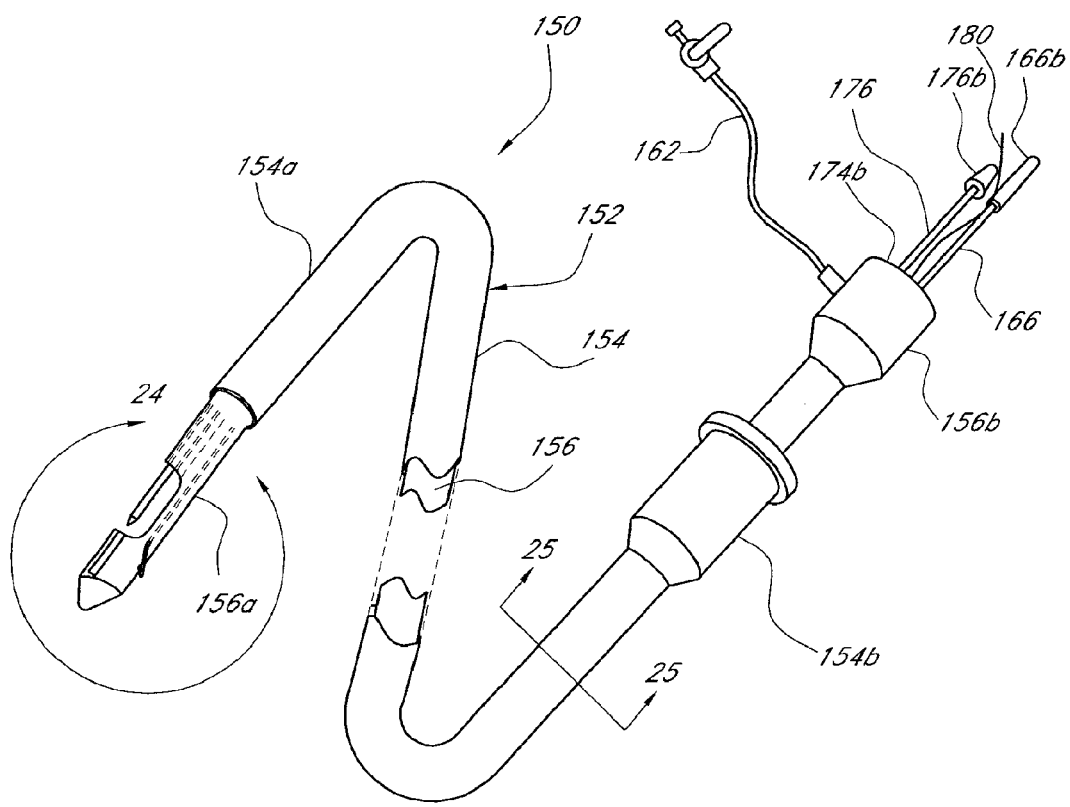
FIG. 23 is a cross-sectional view of yet another modification of the tissue remodeling system of FIG. 1. The system of FIG. 23 includes a catheter configured to deliver a suture into the wall of the left ventricle and including an access catheter body and a suture delivery catheter body.
Figure 24:
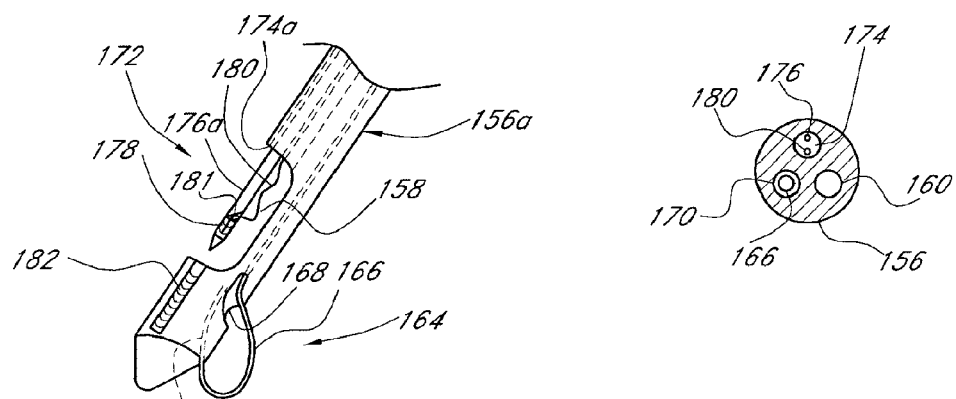
FIG. 24 is an enlarged view of a distal end of the catheter of FIG. 23.
Figure 25:
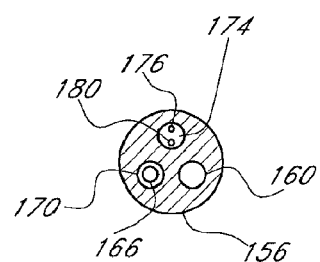
FIG. 25 is a cross-sectional view of the catheter of FIG. 23 taken along the view line 25-25 of FIG. 23.

With reference to FIG. 22, the tissue anchor 110 is shown in its tissue remodeling orientation configured to reduce the volume of the left ventricle LV of the patient's heart H. Once the retaining sleeve 134 is positioned as desired on the tissue anchor 110, the pusher catheter 142 and guide wire 108 may be removed, leaving the tissue anchor 110 implanted in place in the left ventricle LV. If desired, more than one tissue anchor 110 may be deployed using a similar method to create a plurality of tissue folds, depending on the level of remodeling or volume-reduction desired. The multiple tissue anchors 110 may be arranged relative to one another in any suitable orientation to achieve a desired degree or shape of tissue remodeling. For example, the tissue anchors 110 may be arranged along a line generally passing through the tissue area that is desired to be remodeled.

FIGS. 23-31 illustrate another embodiment of a tissue remodeling system generally referred to by the reference numeral 150. The tissue remodeling system 150 is configured to deliver a suture to soft tissue of a patient to facilitate remodeling of the soft tissue of a patient. Preferably, a plurality of sutures are delivered to accomplish the tissue remodeling. The illustrated system 150 is configured to remodel of the left ventricle of a patient's heart and, preferably, to reduce the volume of the left ventricle using a percutaneous approach through the patient's vasculature. Preferably, the vasculature is accessed through an insertion site in the patient's femoral artery. In addition, other remodeling, tissue joining or tying can be accomplished with the illustrated system 150 or modifications thereof.

The illustrated system 150 includes a catheter assembly 152 including a guide catheter, or access catheter 154, and a suture delivery catheter 156, which is axially slidable within the access catheter 154. The catheter assembly 152 is configured to be insertable into a patient's vasculature and, preferably, directed to the patient's left ventricle to facilitate a remodeling of the ventricle.

The access catheter 154 preferably includes a distal end 154a configured to be insertable into the patient's left ventricle. The proximal end 154b of the access catheter 154 is configured to remain outside of the patient and, preferably, defines a handle. The access catheter 154 may be constructed from any suitable material, as described above, and may be of any suitable size and shape. In the illustrated embodiment, the access catheter 154 has an outer diameter of up to about 26F and an inner (lumen) diameter of about 23F. In addition, if desired, the access catheter 154 may be steerable, as described in connection with the catheter 54 of FIGS. 1-3.

The suture delivery catheter 156 includes a distal end portion 156a that is configured to deliver an end of a suture through the soft tissue of a patient and, preferably, permit the end of the suture to be removed from the patient along with the catheter 156. A proximal end 156b of the suture delivery catheter 156 is configured to be exposed from the access catheter 154 and, preferably, defines a handle. The suture delivery catheter 156 may be constructed from any suitable material, as described above, and may be of any suitable size or shape. In the illustrated arrangement, the catheter 156 may have an outer diameter of about 22F. However, the catheter 156 may be constructed with other suitable dimensions as well.

The distal end 156a of the suture delivery catheter 156 preferably defines a cavity, or recess 158, which is configured to receive a portion of the wall of the patient's left ventricle. In one arrangement, the recess 158 may be generally semi-cylindrical in shape. Once the soft tissue is positioned within the recess 158, the suture delivery catheter 156 is configured to permit an end of the suture to be passed through the tissue.

Preferably, the recess 158 is sized such that the suture passes through an inner surface of the wall of tissue, without passing through the outer surface of the wall. To assist in positioning tissue within the recess 158, preferably, a vacuum passage 160 communicates with the recess 158 at one end and extends through a wall of the suture delivery catheter 156 to the proximal end 156b. A vacuum source 162 preferably is connected to the vacuum passage 160 by a suitable connection.

Preferably, the catheter 152 also includes a stabilizer mechanism 164 that is configured to assist in stabilizing the catheter 152 within the left ventricle while the suture is being passed through the wall of the left ventricle. The stabilizer mechanism 164 may also be useful to assist in positioning the distal end 152a of the catheter 152. The illustrated stabilizer mechanism 164 includes a stabilizer wire 166, a portion of which is exposed in the form of a loop near a distal end 156a of the suture delivery catheter 156. A distal end 166a of the stabilizer wire 166 preferably is embedded in a distal end 156a of the suture delivery catheter 156. From the distal end, 166a, the stabilizer wire 166 extends in a loop external to the suture delivery catheter 156 until it passes into an opening 168 in the suture delivery catheter 156 and extends to a proximal end of the suture delivery catheter 156 through a passage 170.

A proximal end of the stabilizer wire 166 defines a handle. Thus, a user may push the handle of the proximal end 166b of the stabilizer wire 166 to enlarge the size of the loop of the stabilizer wire 166 at the distal end 156a of the suture delivery catheter 156. Conversely, if the handle of the proximal end 166b of the stabilizer wire 166 is pulled away from the proximal end 156b of the suture delivery catheter 156, the size of the loop is reduced. The stabilizer wire 166 may be manipulated to vary size of the exposed loop to press against an inner surface of the left ventricle to maintain the distal end 156a of the suture delivery catheter 156 in contact with a wall of the left ventricle. Furthermore, preferably, the stabilizer wire 166 may be retracted completely, or nearly completely, within the suture delivery catheter 156 so as not to interfere with movement of the catheter 156 within the access catheter 154.

Preferably, the system 150 also includes a suture delivery device 172. The suture delivery device 172 preferably includes a passage 174 defined by the body of the suture delivery catheter 156. Preferably, a distal end 174a of the suture passage 174 communicates with the recess 158 and a proximal end 174b of the suture passage 174 opens from a proximal end of the suture delivery catheter 156.

A push rod 176 extends through the suture passage 174. A distal end 176a of the push rod 176 carries a releasable tissue penetration member, or needle 178, which is configured to carry one end of a suture 180. A proximal end 176b of the push rod 176 defines a handle that is external of the suture delivery catheter 156. Thus, the suture passage 174 preferably is sized and shaped to accommodate both a suture 180 and the push rod 176. In the illustrated arrangement, the suture passage 174 may have a diameter of about 0.065 inches to accommodate a push rod 176 having a diameter of about 0.045 inches (17 L Gauge). However, the passage 174 and push rod 176 may have other suitable dimensions to suit a desired application.

In the illustrated arrangement, the needle 178 and the push rod 176 are connectable by a snap-fit arrangement, which is configured to retain the needle 178 on the push rod 176, once assembled, and permit the needle 178 to be selectively removed from the push rod 176 upon application of a sufficient removal force. Furthermore, an end of the suture 180 may be coupled to the needle 178 in any suitable manner. In the illustrated embodiment, the suture passes through an aperture 181 in the push rod 176 (FIG. 24) before being secured to the needle 178.

The suture delivery catheter 156 preferably also defines a needle trap 182 on an end of the recess 158 opposite the suture passage 174. Desirably, the needle trap 182 is aligned with the suture passage 174 such that the needle 178 will enter the trap 182 once it has passed through the recess 158. In the illustrated arrangement, the need trap 182 is an elongate passage configured to receive the needle 178 and inhibit the needle 178 from being released from the trap 182. The needle trap 182 may be of any suitable construction to permit the needle 178 to enter the trap 182 in a first direction and inhibit the needle 178 from being removed. In one arrangement, the trap 182 may comprise one or more oriented ribs, barbs or surface features that exhibit slight resistance to entry of the needle 178, but exhibit significantly greater resistance to the removal of the needle 178. In addition, other suitable arrangements may also be used.

Thus, once positioned within the trap 182, the needle 178 remains in the trap 182 and is disconnected from the push rod 176 as the push rod 176 is retracted from the suture delivery catheter 156. Thus, the needle 178 and suture 180 may be pushed through the tissue occupying the recess 158, entering the tissue at a first location and exiting the tissue at a section location, until the needle 178 is received within the trap 182. The push rod 176 may then be retracted from the suture delivery catheter 156 leaving the needle 178 within the trap 182 and the suture 180 extending through the tissue. The suture 180 may be pulled through the tissue along with the suture delivery catheter 156 as the suture delivery catheter 156 is removed from the left ventricle, as is described in greater detail below. As a result, both ends of the suture 180 will be external the patient, with the suture passing through a section of tissue. Applying tension to both ends of the suture 180 will tend to draw the tissue portions associated with the entry and exit locations of the suture 180 towards one another.

Figure 26:
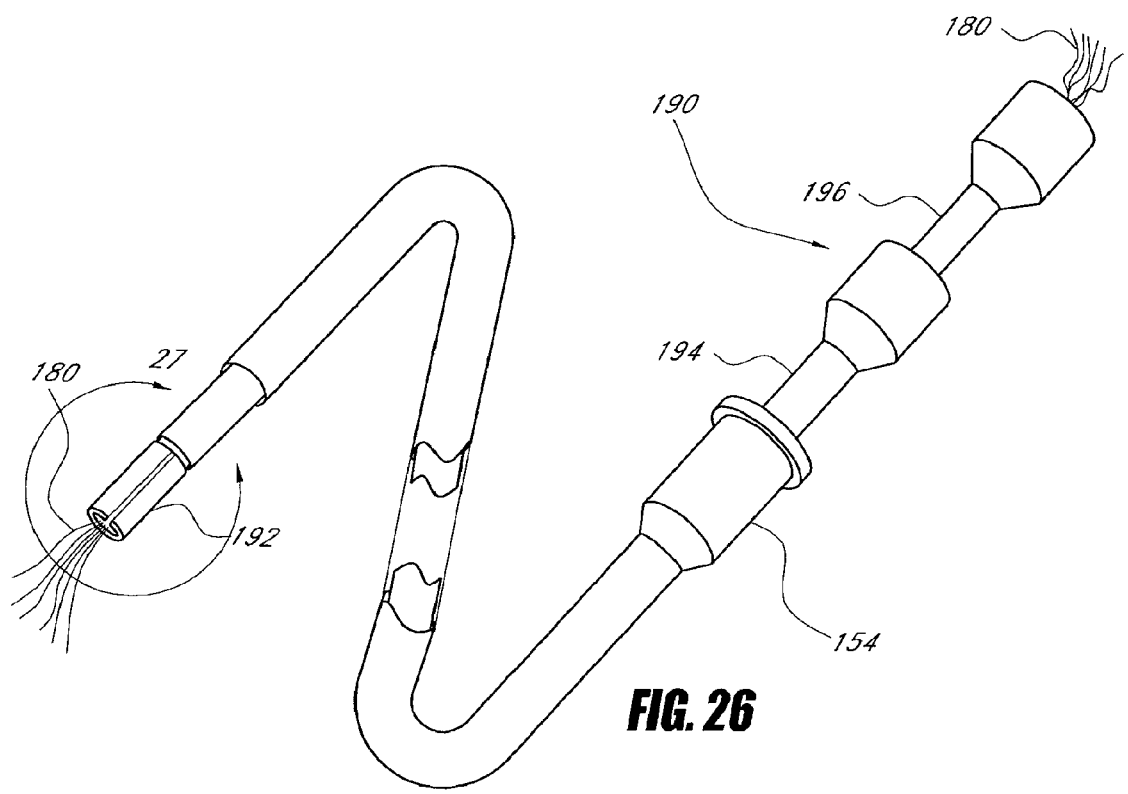
FIG. 26 is a perspective view of the guide catheter of FIG. 23 having the suture delivery catheter replaced by a clip delivery catheter that is configured to deliver a retaining clip.
Figure 27:
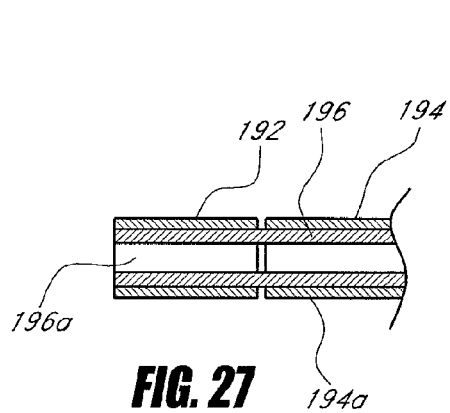
FIG. 27 is a cross-sectional view of a distal end portion of the clip delivery catheter of FIG. 26.
Figure 28:
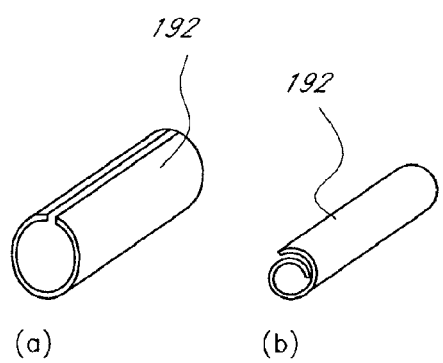
FIG. 28a is a perspective view of the clip removed from the delivery catheter and illustrated in a biased open position.
FIG. 28b is a perspective view of the clip of FIG. 28a in a relaxed position.

With reference to FIGS. 26-28, the tissue remodeling system 150 also includes a catheter 190 configured to deliver a retaining clip 192, which is configured to retain at least one suture 180, and preferably a plurality of sutures 180, in a gathered position, as is described in greater detail below. The retaining clip delivery catheter 190 preferably includes an outer catheter body 194 and an inner catheter body 196. The outer catheter 194 and inner catheter 196 are coaxial with one another and configured to cooperate to deliver the retaining clip 192 through the access catheter 154. In the illustrated arrangement, the outer catheter 194 may have an outer diameter of about 22F, with a lumen of about 17F. The inner catheter 196 may have an outer diameter of about 12 to 14F, with a lumen of about 10F. Other suitable dimensions may be used to suit an individual application.

With reference to FIG. 27, preferably, the retaining clip 192 is supported on a distal end portion 196a of the inner catheter 196. A distal end portion 194a of the outer catheter 194 is positioned adjacent the retaining clip 192. The outer catheter 194 is movable relative to the inner catheter 196 to selectively push the retaining clip 194 off of the distal end 196a of the inner catheter 196.

With reference to FIGS. 28a and 28b, desirably the retaining clip 192 is formed from a shape memory material, such as NiTi, for example, such that the clip 192 is moveable from a biased opened position, such as when supported on the inner catheter 196, to a relaxed position, wherein the retaining clip 192 coils over on itself, as illustrated in FIG. 28b. When in its relaxed position, the retaining clip 192 is configured to retain one or more sutures 180 in a gathered orientation, as is described in greater detail below.

Figure 29:
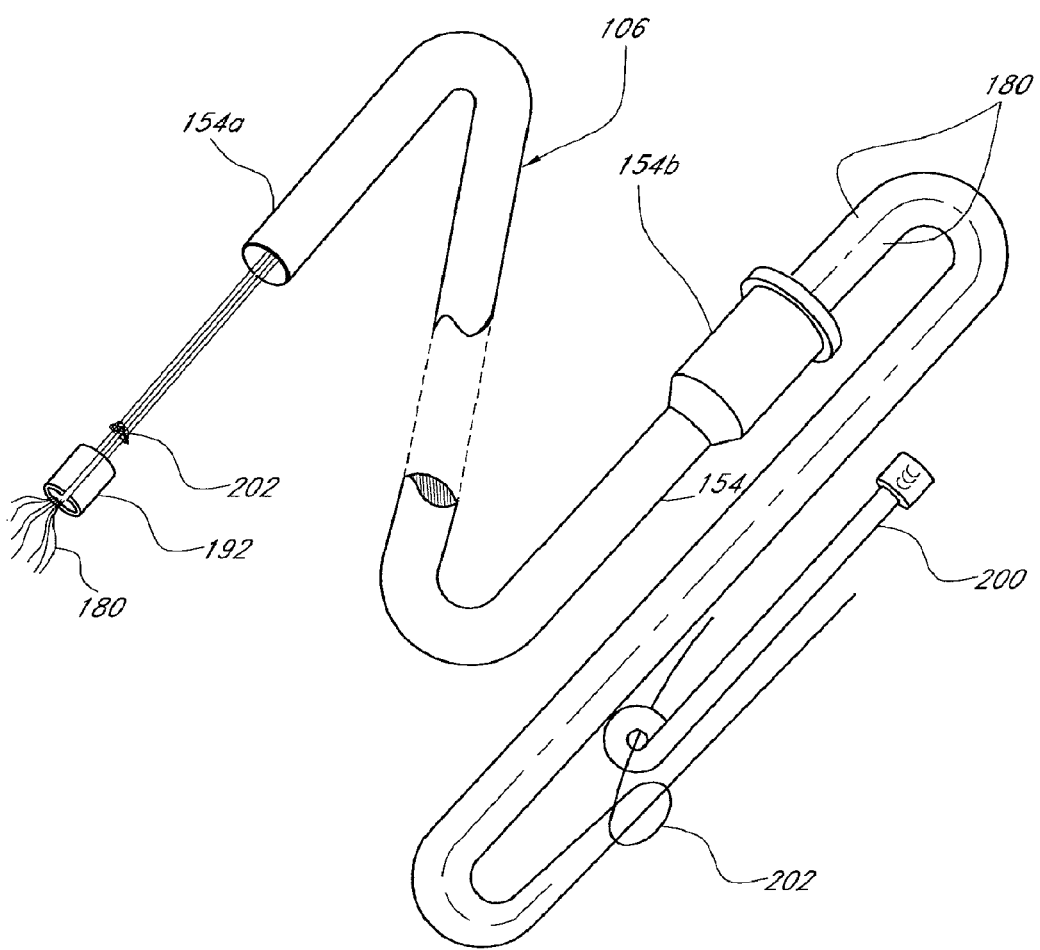
FIG. 29 is a perspective view of the access catheter of FIG. 23 and a knot pusher which may be used to push a knot in the suture from an exposed end of the suture through the catheter to a position behind the retaining clip.
Figure 30:
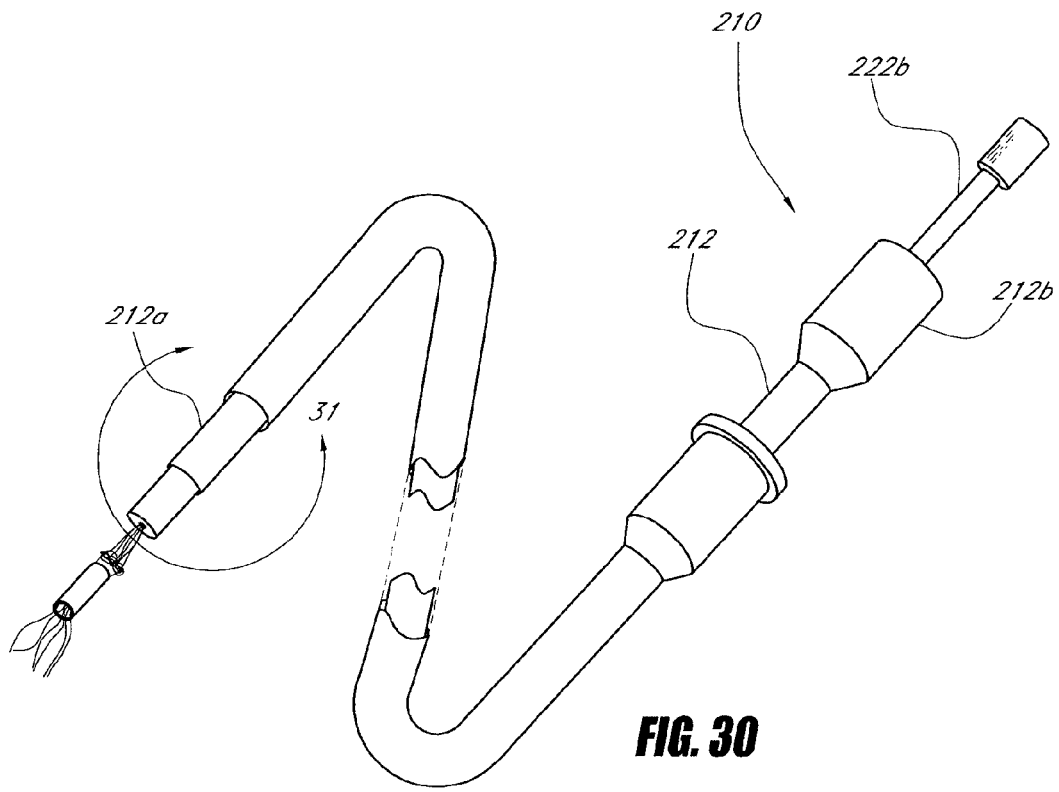
FIG. 30 is a perspective view of the access catheter of FIG. 23 with the suture delivery catheter replaced by a suture cutting catheter.
Figure 31:
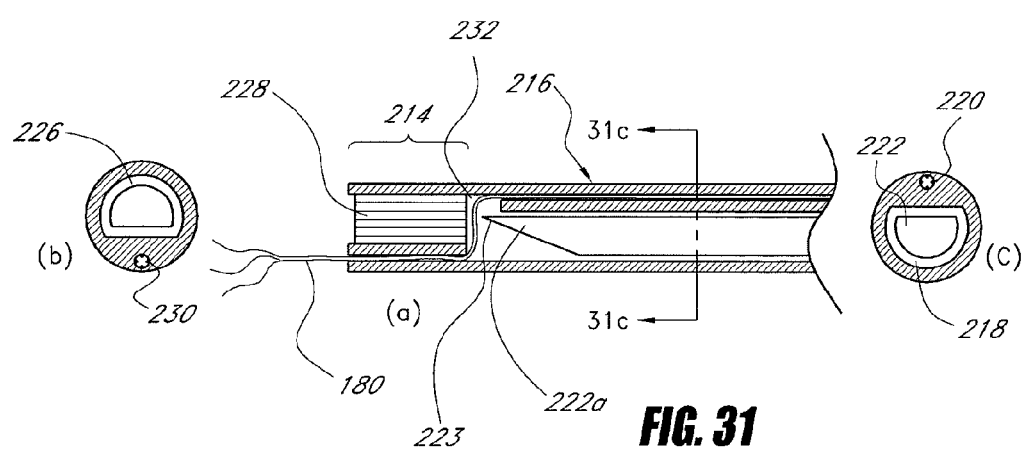
FIGS. 31a-c are several views of a distal end portion of the suture cutting catheter of FIG. 30 indicated by the view line 31 of FIG. 30.

With reference to FIG. 29, preferably, both the suture delivery catheter 156 and the retaining clip delivery catheter 190 may be removed from the access catheter 154. A knot pusher 200 may be used to push a knot 202 from external a proximal end 154b of the access catheter 154 to external a distal end 154a of the access catheter 154 and, preferably, against the retaining clip 192. Thus, one or more knots 202 may be used to inhibit, or prevent, the retaining clip 192 from moving relative to the sutures 180 to advantageously retain the sutures 180 in a gathered orientation. The knot pusher 200 preferably is of a conventional construction comprising an elongate body of stainless steel having distal tip formed into a loop, as will be appreciated by one of skill in the art. Other suitable methods or devices to move a knot 202 along the sutures 180 or otherwise inhibit undesired movement of the retaining clip 192 may also be used.

The tissue remodeling system 150 preferably also includes a suture cutting device 210. The suture cutter assembly 210 preferably includes a catheter 212 having a distal end 212a and a proximal end 212b. Desirably, the proximal end 212b defines a handle. The catheter 212 preferably includes a distal end section 214 and a proximal end section 216. Preferably, the proximal end 216 includes a semi-cylindrical passage 218 and a suture passage 220. A push rod 222 extends through the passage 218 and, preferably, is also semi-cylindrical in shape to generally match the shape of the passage 218. A distal end 222a of the push rod 222 preferably includes a cutting surface 223 and a proximal end 222b of the push rod defines a handle.

The distal end section 214 preferably also includes a semi-cylindrical passage 226 that is closed by a plug 228. Further, the distal end section 214 preferably includes a suture passage 230. In the illustrated arrangement, the distal end section 214 defines a working space 232 between the passage 226 and suture passage 230 of the distal end section 214 and the passage 218 and suture passage 220 of the proximal end section 216. Desirably, the distal end section 214 is oriented such that the suture passage 220 and the suture passage 230 are directly opposite one another. The suture 180 may be passed through the passages 220 and 230 so that the suture 180 will pass through the working space 232 past the cutting surface 223 of the push rod 222. The push rod 222 may be advanced to cut the suture between the cutting surface 223 and the distal end 222a and the plug 228. Alternatively, the distal end section 214 may be rotatable relative to the proximal section 216 such that the suture passages 220 and 230 may be selectively aligned, the suture passed through the passages 220 and 230, and the distal end section 214 rotated relative to the proximal section 216 such that the suture passages 220 and 230 are opposite one another so that the suture may be cut. In addition, other suitable devices or methods may also be used to cut the one or more sutures 180, if desired.

Figure 32:
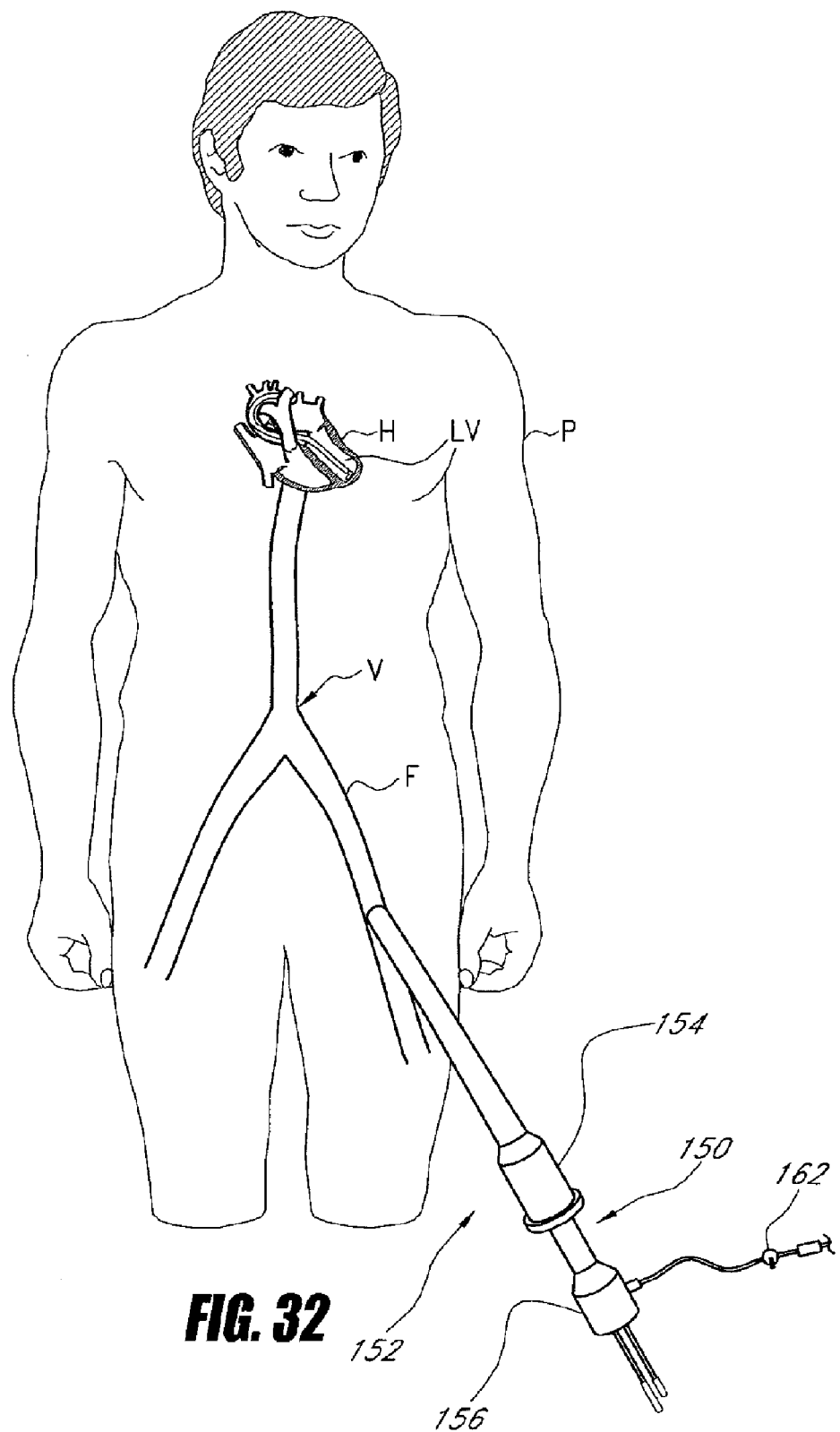
FIG. 32 is a schematic illustration of the tissue remodeling system of FIGS. 23-31 being introduced into a patient to remodel the left ventricle of the patient's heart by accessing the patient's vasculature through the femoral artery.

With reference to FIGS. 32-40, a preferred method of remodeling tissue with the system 150 of FIGS. 23-31 is illustrated. As described above, the preferred method is utilized to reduce a volume of the left ventricle LV of the heart H of a patient P. With reference to FIG. 32, desirably, the system 150 is configured to be introduced into the vasculature V of the patient P at a desired site. In the illustrated arrangement, the catheter 152 is introduced through the femoral artery F of the patient P and is guided to the left ventricle LV.

Figure 33A:
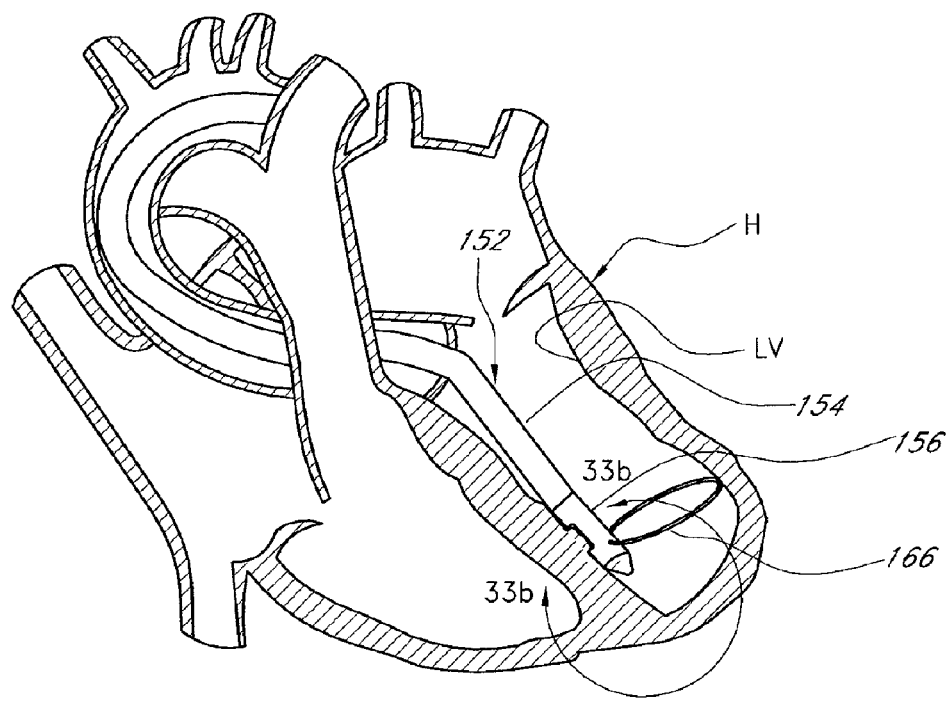
FIG. 33a is a cross-sectional view of the patient's heart illustrating the system delivering a suture through a wall of the left ventricle.
Figure 33B:
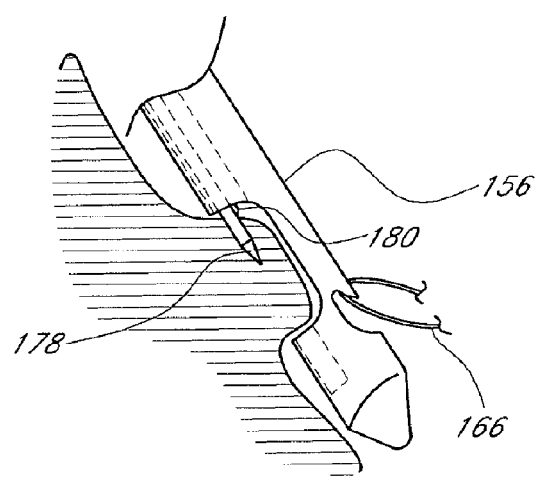
FIG. 33b is an enlarged view of the distal end of the suture delivering catheter.

With additional reference to FIGS. 33a and 33b, the suture delivery catheter 156 is positioned within the left ventricle LV so that the suture may be passed through a desired site of the wall of the left ventricle LV. The suture delivery catheter 156 may be positioned by steering one or both of the access catheter 154 and suture delivery catheter 156. In addition, the stabilizing wire 166 may be used to assist in positioning the suture delivery catheter 156 and retaining the suture delivery catheter 156 in a desired position within the left ventricle LV.

Once positioned as desired, the vacuum source 162 may be activated to draw tissue within the recess 158 (FIG. 24) of the suture delivery catheter 156. The push rod 166 may then be advanced to push the needle 178 through the tissue occupying the recess 158. The push rod 166 preferably is advanced until the needle 178 enters the trap 182 whereby the suture 180 is passed through the tissue within the recess 158.

Figure 34A:
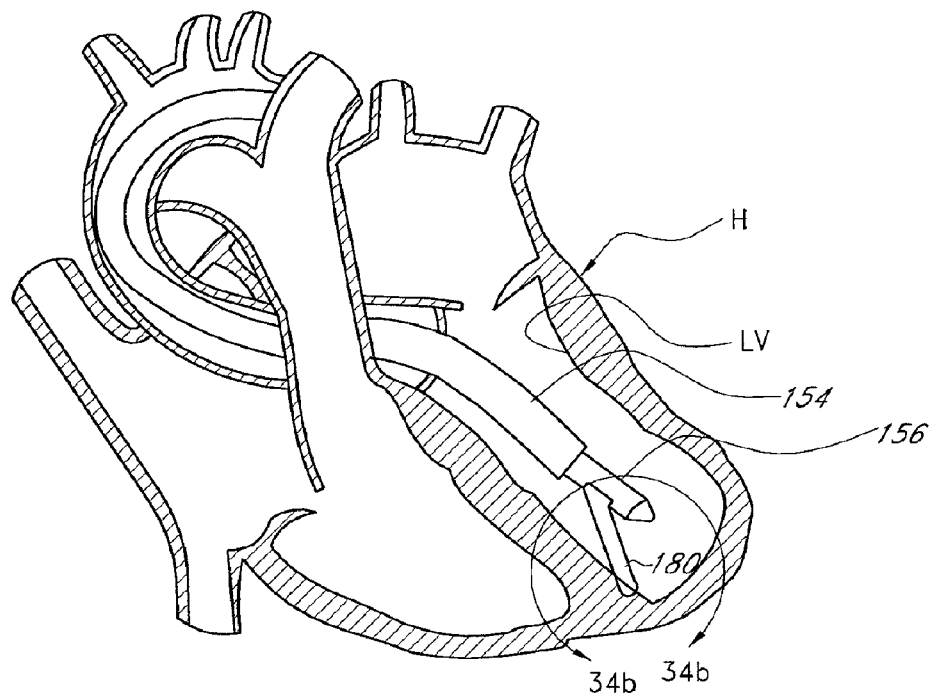
FIG. 34a is a cross-sectional view of the patient's heart illustrating the suture delivered through the wall of the left ventricle and the catheter released from the wall of the heart.
Figure 34B:
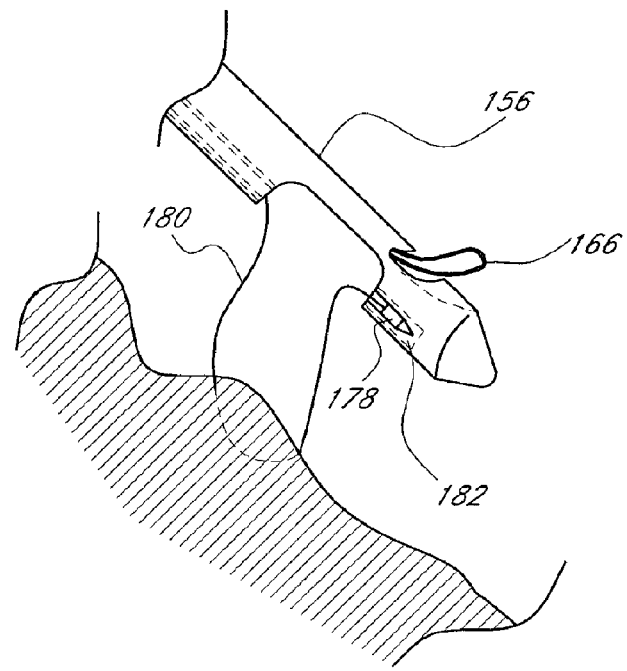

With reference FIG. 34a and 34b, the stabilizing wire 166 may be retracted and the vacuum source 162 deactivated. The suture delivery catheter 156 may be withdrawn thereby pulling the suture 180 through the tissue and removing the end of the suture 180 along with the suture delivery catheter 156. Thus, once the suture delivery catheter 156 is completely removed from the patient's vasculature, both ends of the suture 180 will be external the patient with the suture 180 passing through a section of the tissue of the left ventricle LV, entering the tissue at a first location and exiting the tissue at a second location spaced from the first location.

Figure 35:
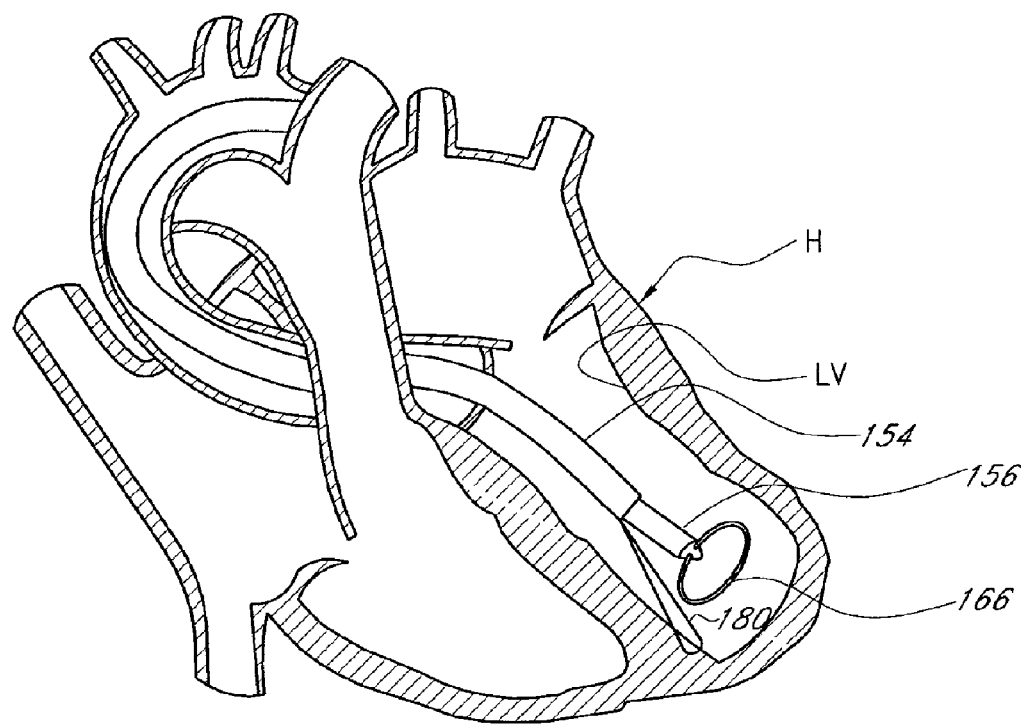
FIG. 35 is a cross-sectional view of the patient's heart illustrating the suture delivery catheter delivering another suture to the ventricle wall.
Figure 36:
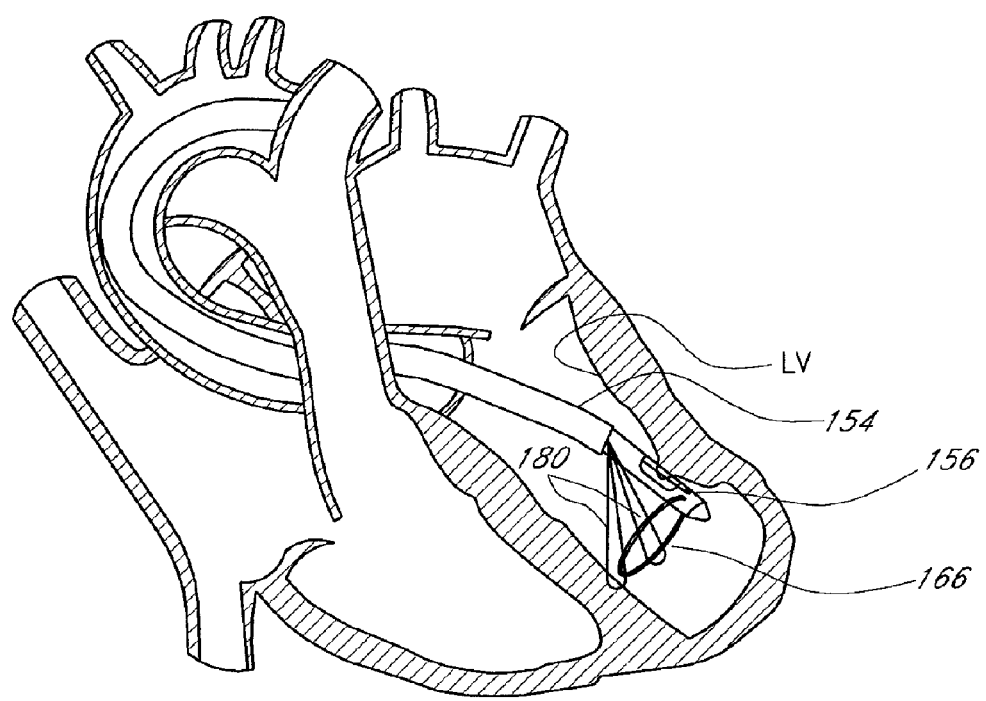
FIG. 36 is a cross-sectional view of the patient's heart illustrating the suture delivery catheter delivering yet another suture to the ventricle wall.

With reference to FIG. 35 and 36, preferably additional sutures 180 are positioned within the left ventricle in desired positions relative to the initial suture 180. Preferably, the multiple sutures 180 are positioned such that, when drawn together, the tissue of the left ventricle will be drawn together along a desired suturing line around the diseased portion of the ventricle, which will reduce the volume of the ventricle. However, in some arrangements, a desired level of remodeling, tying or tissue joining may be accomplished with only one suture 180.

Figure 37:
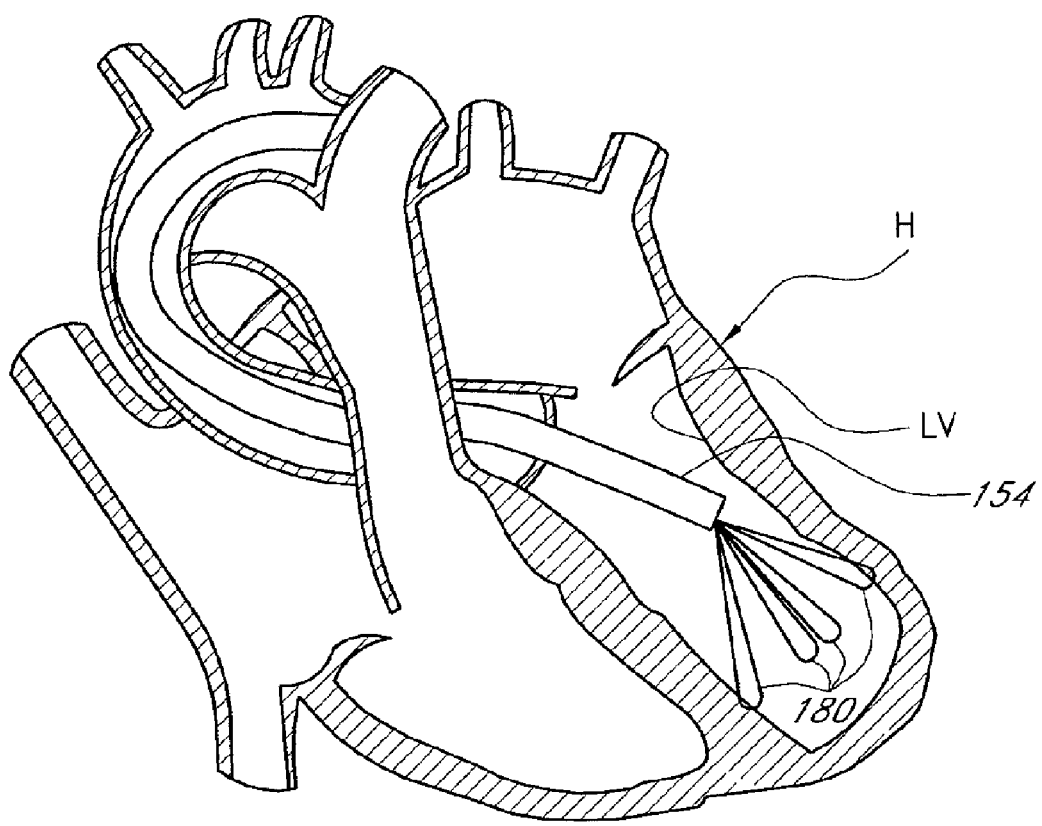
FIG. 37 is a cross-sectional view of the patient's heart illustrating multiple sutures implanted in the ventricle wall with both free ends of the sutures extending through the access catheter.
Figure 38:
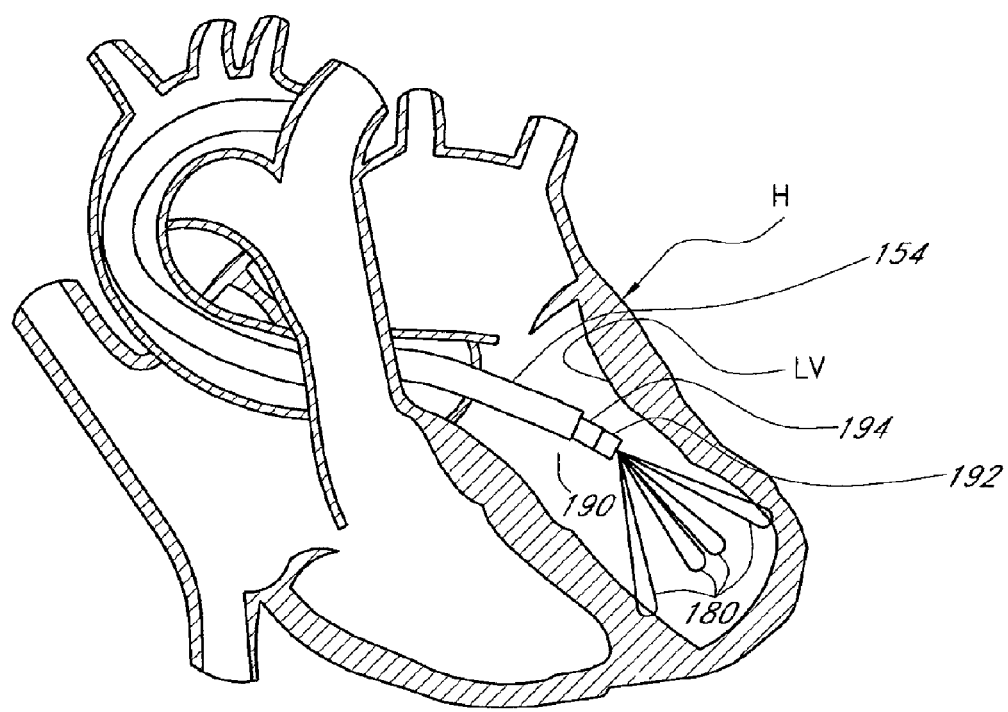
FIG. 38 is a cross-sectional view of the patient's heart illustrating the clip delivery catheter of FIG. 26 delivering a retaining clip onto the sutures.
Figure 39:
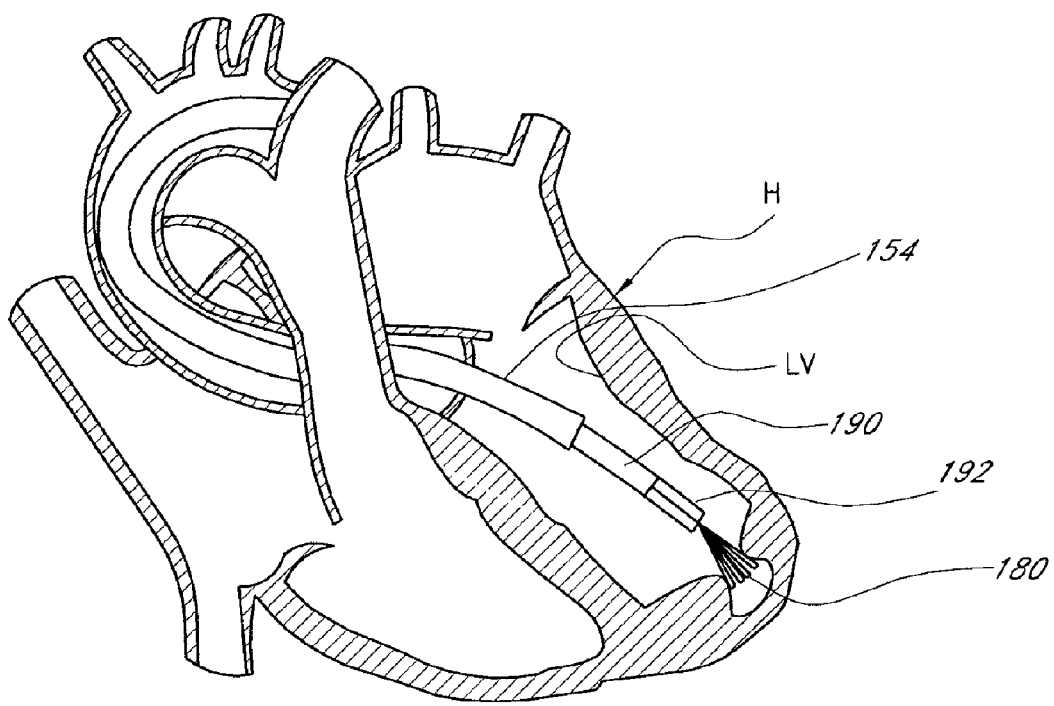
FIG. 39 is a cross-sectional view of the patient's heart illustrating the retaining clip gathering the sutures to draw tissues portion of the ventricle toward one another and reducing the volume of the ventricle.

With references to FIGS. 37-39, once a desired number of sutures 180 are placed within the left ventricle LV, the retaining clip delivery catheter 190 is advanced over the sutures 180 and within the access catheter 154 until a distal end of the retaining clip delivery catheter 190 is within the left ventricle LV. The retaining clip delivery catheter 190 is advanced until the sutures 180 are drawn together to reduce the volume of the left ventricle LV, preferably much like the closing of a pursestring suture. When the sutures 180 are drawn together to a sufficient degree, the outer catheter 194 may be advanced relative to the inner catheter 196 such that the retaining clip 192 is deployed therefrom, preferably substantially as described above with reference to FIG. 27.

Figure 40:
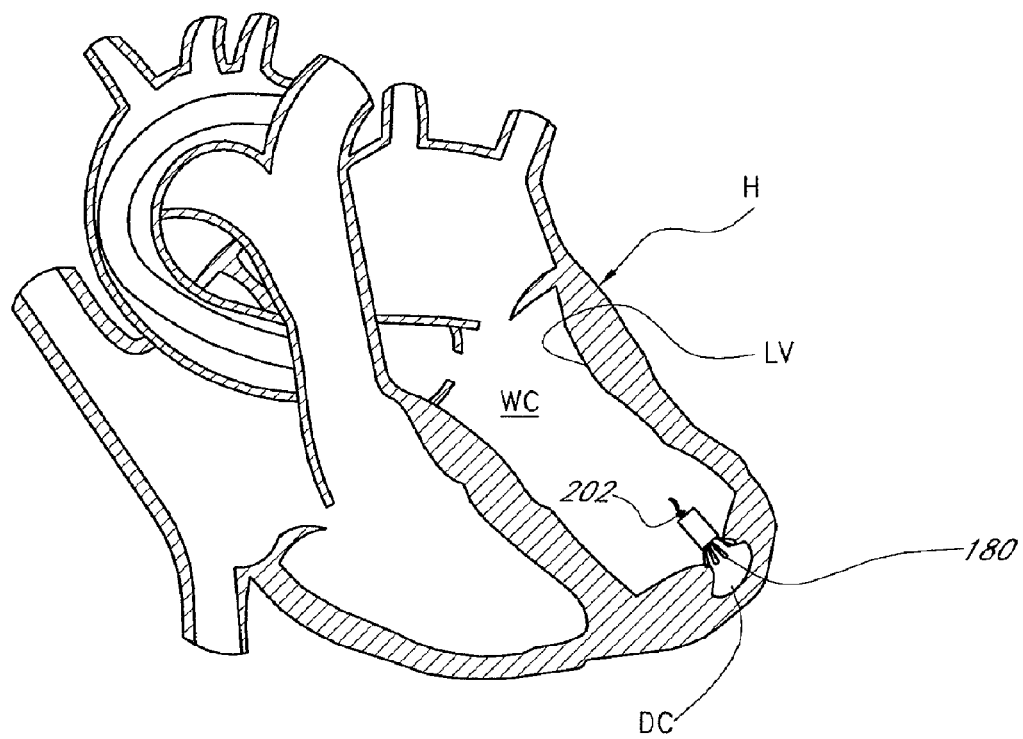
FIG. 40 is a cross-sectional view of the patient's heart illustrating the gathered sutures and retaining clip secured by knots in the sutures behind the retaining clip. The ends of the sutures are cut behind the knots, preferably by a device such as the suture cutting catheter of FIG. 30.

FIG. 40 illustrates the gathered sutures retained by the retaining clip 192 such that the volume of the left ventricle LV is reduced. Preferably, the left ventricle LV is reduced to a volume that approximates the normal size of the ventricle prior to the onset of heart disease, or that results in an acceptable level of performance. In one arrangement, the dyskinetic portion of the left ventricle LV is essentially eliminated from defining the working chamber of the ventricle LV. If the dyskinetic portion of the ventricle LV is large enough, the plurality of sutures 180, in a drawn together orientation, create two chambers within the ventricle: a working chamber WC and a dormant chamber DC. Preferably, the sutures 180 draw the wall of the ventricle together to an extent that the chambers WC and DC are substantially isolated from one another. That is, although some minor amount of fluid communication may exist between the chambers WC and DC, the dormant chamber DC does not effectively contribute to the working volume of the ventricle LV.

As illustrated, preferably, a plurality of knots 202 are created within the sutures 180 and advanced to a position behind the retainer clip 192 to retain the sutures 180 in a drawn together position. Preferably, the knots 202 are advanced from external the patient P to behind the retainer clip 192 by a knot pusher, such as the knot pusher 200 described in relation to FIG. 29. However, other suitable methods or devices for creating knots, or otherwise retaining the retainer clip 192 in a desired position, may also be used. In addition, the ends of the sutures 180 are cut, preferably using a device substantially as described with respect to FIGS. 30 and 31. However, other suitable methods or devices for cutting the sutures 180 may also be used.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In particular, while the present tissue remodeling systems and methods have been described in the context of particularly preferred embodiments, the skilled artisan will appreciate, in view of the present disclosure, that certain advantages, features and aspects of the system may be realized in a variety of other applications, many of which have been noted above. Additionally, it is contemplated that various aspects and features of the invention described can be practiced separately, combined together, or substituted for one another, and that a variety of combination and subcombinations of the features and aspects can be made and still fall within the scope of the invention. Thus, it is intended that the scope of the present invention herein disclosed should not be limited by the particular disclosed embodiments described above, but should be determined only by a fair reading of the claims.

What is claimed is:

1. A method of reducing the volume of a heart ventricle, comprising:
    introducing a catheter into the heart ventricle though the aorta;
    advancing a tissue-penetrating tip of said catheter to penetrate an interior surface of the ventricle wall;
    creating a channel within said wall by further advancing said catheter;
    depositing a tissue-remodeling clip within said channel, said clip having a first end and a second end, said first and second ends resiliently biased to move towards one another to move associated first and second tissue portions of the ventricle wall toward one another, thereby reducing the volume of the ventricle;
    wherein said catheter comprises an access catheter body and a delivery catheter body, the method additionally comprising positioning a distal end surface of said access catheter body adjacent a desired implantation site on the ventricle wall and inflating an annular balloon carried by a distal end of said access catheter body, said balloon configured to space said distal end surface away from the ventricle wall.

2. A method of reducing the volume of a heart ventricle, comprising:
    introducing a catheter assembly into the heart ventricle through the aorta, said catheter assembly comprising an access catheter and a delivery catheter;
    aligning a distal end of said catheter assembly with a desired remodeling site of a wall of the ventricle with a distal end surface of said catheter assembly spaced from an interior surface of the ventricle wall;
    advancing said delivery catheter from said access catheter to at least partially expose a tissue anchor carried by said delivery catheter, wherein a plurality of legs of said tissue anchor tend to spread apart from one another when exposed from said access catheter;
    advancing said delivery catheter toward the ventricle wall until a tissue-penetrating tip of each of said plurality of legs of said tissue anchor penetrate the interior surface of the ventricle wall;
    moving said plurality of legs toward one another to a tissue-remodeling position wherein tissue portions associated with each of said plurality of legs are moved toward one another; and
    retaining said plurality of legs in said tissue-remodeling position, wherein said retaining said plurality of legs in said tissue-remodeling position is accomplished by advancing a retaining member over said tissue anchor.

3. The method of claim 2, wherein both said moving of said plurality of legs to said tissue-remodeling position and said retaining of said plurality of legs in said tissue-remodeling position are accomplished by advancing a retaining member over said tissue anchor.

4. The method of claim 2, wherein said advancing of said retaining member over said tissue anchor is accomplished with a catheter other than said access catheter and said delivery catheter.

5. The method of claim 2, additionally comprising introducing a guide wire into the heart ventricle through the aorta and utilizing said guide wire for said introducing of said delivery catheter and said access catheter.

6. The method of claim 2, wherein said moving of said tissue portions comprises moving at least three tissue portions towards one another.

7. A method of treating a heart, comprising:
    introducing a catheter into the heart ventricle through the aorta;
    positioning said catheter adjacent an interior surface of a wall of the ventricle;
    passing at least one suture through the interior surface of the wall of the ventricle, said passing comprising passing said at least one suture through said interior surface at at least three pairs of tissue penetration locations, each of said pairs being spaced from the other of said pairs;
    drawing tissue at said pairs of tissue penetration locations towards each other by applying force to said at least one suture, said pairs spaced such that said drawing gathers tissue within the ventricle to treat the heart.

8. The method of claim 7, wherein said treating of the heart comprises reducing a volume of the ventricle.

9. The method of claim 7 wherein no suture penetrates an outer surface of the ventricle.

10. The method of claim 7 comprising a first suture, a second suture, and a third suture, wherein:
    said at least three pairs of tissue penetration locations comprises a first pair of tissue penetration locations, a second pair of tissue penetration locations, and a third pair of tissue penetration locations;
    said first suture passes through said first pair of tissue penetration locations, said second suture passes through said second pair of tissue penetration locations, and said third suture passes through said third pair of tissue penetration locations.

11. The method of claim 10 wherein:
    said second suture is passed through said interior surface at said second pair of tissue penetration locations after said first suture has been passed through said interior surface at said first pair of tissue penetration locations;
    said third suture is passed through said interior surface after said second suture is passed through said interior surface at said second pair of tissue penetration locations.

12. The method of claim 7 wherein:
said at least three pairs of tissue penetration locations comprises a first pair of tissue penetration locations, a second pair of tissue penetration locations, and a third pair of tissue penetration locations;
said first pair of tissue penetration locations is adjacent to said second pair of tissue penetration locations, and a said second pair of tissue penetration locations is adjacent to said third pair of tissue penetration locations.

13. A method of reducing the volume of a heart ventricle, comprising:
introducing a catheter assembly into the heart ventricle through the aorta, said catheter assembly comprising an access catheter and a delivery catheter;
aligning a distal end of said catheter assembly with a desired remodeling site of a wall of the ventricle with a distal end surface of said catheter assembly spaced from an interior surface of the ventricle wall;
advancing said delivery catheter from said access catheter to at least partially expose a tissue anchor carried by said delivery catheter, wherein a plurality of legs of said tissue anchor tend to spread apart from one another when exposed from said access catheter;
advancing said delivery catheter toward the ventricle wall until a tissue-penetrating tip of each of said plurality of legs of said tissue anchor penetrate the interior surface of the ventricle wall;
moving said plurality of legs toward one another to a tissue-remodeling position wherein tissue portions associated with each of said plurality of legs are moved toward one another; and
retaining said plurality of legs in said tissue-remodeling position;
wherein each of said plurality of legs of said tissue anchor is biased to spread apart from one another when exposed from said access catheter.

14. The method of claim 13, wherein said plurality of legs of said tissue anchor can be retained in any selected one of a multiple number of positions.

15. The method of claim 13, wherein three or more tissue portions of the ventricle are moved toward one another.

16. The method of claim 13, comprising an annular member to retain said plurality of legs in said tissue-remodeling position.

* * * * *

UNITED STATES PATENT AND TRADEMARK OFFICE
CERTIFICATE OF CORRECTION

Figure 11E:
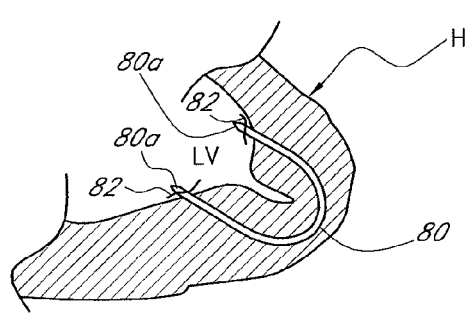
FIG. 11e is a view of the clip of FIGS. 7a-d implanted into the wall of the ventricle and in a tissue remodeling position.

PATENT NO. : 7,452,325 B2  Page 1 of 1
APPLICATION NO. : 11/059866
DATED : November 18, 2008
INVENTOR(S) : Laurent Schaller It is certified that error appears in the above-identified patent and that said Letters Patent is hereby corrected as shown below:

At column 10, line 58, please delete "FIG. 11c" and insert therefore, --FIG. 11b--.
    At column 11, line 7, please delete "lid" and insert therefore, --11b--.
    At Column 11, lines 24-36, please delete "With reference to FIG. 11c, once the passage has been created within the wall of the left ventricle LV, the push rod 76 may be used to hold the clip 74 in position while permitting the tissue-penetrating catheter 56 to be withdrawn from the passage and into the access catheter 54, thus leaving the clip 74 in place within the passage in the wall of the left ventricle LV. Alternatively, the tissue-penetrating catheter 56 may be withdrawn from the passage, along with the clip 74, and the push rod 76 used to subsequently deploy the clip 74 into the preformed passage. The preferred method of deploying the clip 74 may depend on individual user preference, the shape of the clip 74 or the properties of the soft tissue T, among other considerations." and insert therefore, --In Figures 11a-11d, the implantable clip 74 is illustrated. However, other embodiments of the clip, such as the clips 80 and 90, may be implanted in a similar manner. With reference to Figure 11e, the clip 80 is illustrated as implanted in the wall of the left ventricle LV. In the clip 80, preferably the ends 80a and 80b protrude from an inner surface of the wall of the left ventricle and the pledgets 82 contact the inner surface of the wall of the ventricle LV to inhibit the ends 80a, 80b from withdrawing into the wall of the left ventricle.--.
    At column 17, line 58, please delete "(17 L Gauge)" and insert therefore, --(17 Gauge)--.
    At column 21, line 34, Claim 1, please delete "though" and insert therefore, --through--.

Signed and Sealed this

Twenty-eighth Day of April, 2009

JOHN DOLL
*Acting Director of the United States Patent and Trademark Office*